(12) United States Patent
Sinskey et al.

(10) Patent No.: US 6,884,606 B2
(45) Date of Patent: Apr. 26, 2005

(54) **PYRUVATE CARBOXYLASE FROM *CORYNEBACTERIUM GLUTAMICUM***

(75) Inventors: Anthony J. Sinskey, Boston, MA (US); Philip A. Lessard, Framingham, MA (US); Laura B. Willis, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 179 days.

(21) Appl. No.: 10/045,072

(22) Filed: Jan. 15, 2002

(65) Prior Publication Data

US 2003/0027305 A1 Feb. 6, 2003

Related U.S. Application Data

(62) Division of application No. 09/677,575, filed on Oct. 3, 2000, now Pat. No. 6,403,351, which is a division of application No. 09/220,081, filed on Dec. 23, 1998, now Pat. No. 6,171,833.

(51) Int. Cl.$^7$ ............................. C12P 13/08; C12N 9/00

(52) U.S. Cl. ..................................... 435/115; 435/183

(58) Field of Search .................................. 435/115, 183

(56) References Cited

U.S. PATENT DOCUMENTS

| 4,275,157 A | 6/1981 | Tosaka et al. | 435/115 |
| 6,171,833 B1 | 1/2001 | Sinskey et al. | 435/183 |

FOREIGN PATENT DOCUMENTS

| EP | 0 723 011 | 7/1996 |
| WO | WO 99/18228 | 4/1999 |

OTHER PUBLICATIONS

Altschul, S.F. et al., "Basic Local Alignment Search Tool," *J. Mol. Biol.* 215:403–410, Academic Press, Inc., New York, NY (1990).
Attwood, P.V., "The Structure and the Mechanism of Action of Pyruvate Carboxylase," *Int. J. Biochem. Cell Biol.* 27:231–249, Pergamon Press, Exeter, England (1995).
Brewster, N.K. et al., "Regulation of Pyruvate Carboxylase Isozyme (*PYC1, PYC2*) Gene Expression in *Saccharomyces cerevisiae* during Fermentative and Nonfermentative Growth," *Arch. Biochem. Biophys.* 311:62–71, Academic Press, New York, NY (1994).
Charles, A.M. and Willer, D.W. "Pyruvate carboxylase from *Thiobacillus novellus*: properties and possible function," *Can. J. Microbiol.* 30:532–539, National Research Council Of Canada, Ottawa, Canada (1984).
Dunn, M.F. et al., "Pyruvate Carboxylase from *Rhizobium etli*: Mutant Characterization, Nucleotide Sequence, and Physiological Role," *J. Bacteriol.* 178:5960–5970, American Society for Microbiology, Baltimore, MD (1996).

Fry, D.C. et al., "ATP–binding site of adenylate kinase: Mechanistic implications of its homology with ras–encoded p21, $F_1$–ATPase, and other nucleotide–binding proteins," *Proc. Natl. Acad. Sci. USA* 83:907–911, National Academy of Sciences of the USA, Washington, D.C. (1986).
Gubler, M. et al., "Effects of phosphoenol pyruvate carboxylase deficiency on metabolism and lysine production in *Corynebacterium glutamicum*," *Appl. Microbiol. Biotechnol.* 40:857–863, Springer–Verlag, Berlin, Germany (1994).
Hanahan, D., "Studies on Transformation of *Escherichia coli* with Plasmids," *J. Mol. Biol.* 166:557–580, Academic Press, Inc., New York, NY (1983).
Jäger, W. et al., "A *Corynebacterium glutamicum* gene encoding a two–domain protein similar to biotin carboxylases and biotin–carboxyl–carrier proteins," *Arch. Microbiol.* 166:76–82, Springer–Verlag, Berlin, Germany (1996).
Jetten, M.S.M. and Sinskey, A.J., "Characterization of phosphoenolpyruvate carboxykinkase from *Corynebacterium glutamicum*," *FEMS Microbiol. Lett.* 111:183–188, Elsevier/North Holland, Amsterdam (1993).
Keilhauer, C. et al., "Isoleucine Synthesis in *Corynebacterium glutamicum*: Molecular Analysis of the *ilvB–ilvN–ilvC* Operon," *J. Bacteriol.* 175:5595–5603, American Society for Microbiology, Baltimore, MD (1993).
Koffas, M.A.G. et al., "Sequence of the *Corynebacterium glutamicum* pyruvate carboxylase gene," *Appl. Microbiol. Biotechnol.* 50:346–352, Springer–Verlag, Berlin, Germany (Sep. 1998).
Koffas, M.A.G., et al., GenEmbl database, Accession No. AF038548, alignment results (Sep. 1998).
Kondo, H. et al., "Cloning and nucleotide sequence of *Bacillus stearothermophilus* pyruvate carboxylase," *Gene* 191:47–50, Elsevier Science Publishers B.V., Amsterdam, Netherlands (May 1997).
Kumar, G.K. et al., "Involvement and Identification of Tryptophanyl Residue at the Pyruvate Binding Site of Transcarboxylase," *Biochem.* 27:5978–5983, American Chemical Society, Washington D.C. (1988).
Lim, F et al., "Sequence and Domain Structure of Yeast Pyruvate Carboxylase," *J. Biol. Chem.* 263:11493–11497, American Society for Biochemistry and Molecular Biology, Inc., Baltimore, MD (1988).
Milrad de Forchetti, S.R. and Cazzulo, J.J., "Some Properties of the Pyruvate Carboxylase from *Pseudomonas fluorescens*," *J. Gen. Microbiol.* 93:75–81, Cambridge University Press, Cambridge, England (1976).

(Continued)

Primary Examiner—Maryam Monshipouri
(74) Attorney, Agent, or Firm—Buchanan Ingersoll PC

(57) ABSTRACT

The present invention concerns an anaplerotic enzyme from *Corynebacterium glutamicum* which replenishes oxaloacetate consumed during lysine and glutamic acid production in industrial fermentations. In particular, isolated nucleic acid molecules are provided encoding the pyruvate carboxylase protein. Pyruvate carboxylase polypeptides are also provided.

1 Claim, 3 Drawing Sheets

OTHER PUBLICATIONS

Momose, H. et al., "On the Transducing Phages in Glutamic Acid–Producing Bacteria," *J. Gen. Appl. Microbiol.* 22:119–129, Microbiology Research Foundation, Tokyo, Japan (1976).

Mukhopadhyay, B. et al., "Purification, Regulation, and Molecular and Biochemical Characterization of Pyruvate Carboxylase from *Methanobacterium thermoautotrophicum* Strain ΔH," *J. Biol. Chem.* 273:5155–5166, American Society for Biochemistry and Molecular Biology, Inc., Baltimore, MD (Feb. 1998).

O'Brien, R.W. et al., "Novel Enzymic Machinery for the Metabolism of Oxalacetate, Phosphoenolpyruvate, and Pyruvate in *Pseudomonas citronellolis*," *J. Biol. Chem.* 252:1257–1263, American Society for Biochemistry and Molecular Biology, Inc., Baltimore, MD (1977).

Park, S.M. et al., "Elucidation of anaplerotic pathways in *Corynebacterium glutamicum* via $^{13}$C–NMR spectroscopy and GC–MS," *Appl. Microbiol. Biotechnol.* 47:430–440, Springer–Verlag, Berlin, Germany (Apr. 1997).

Peters–Wendisch, P.G. et al., "Phosphoenolpyruvate carboxylase in *Corynebacterium glutamicum* is dispensable for growth and lysine production," *FEMS Microbiol. Lett.* 112:269–274, Elsevier/North Holland, Amsterdam, Netherlands (1993).

Peters–Wendisch, P.G. et al., "$C_3$–Carboxylation as an anaplerotic reaction in phosphoenolpyruvate carboxylase–deficient *Cornybacterium glutamicum*," *Arch. Microbiol.* 165:387–396, Springer–Verlag, Berlin, Germany (1996).

Peters–Wendisch, P.G. et al., "Pyruvate carboxylase as an anaplerotic enzyme in *Cornybacterium glutamicum*," *Microbiology* 143:1095–1103, Kluwer Academic/Plenum Publishers, Washington, D.C. (Apr. 1997).

Peters–Wendisch, P.G. et al., "Pyruvate carboxylase from *Corynebacterium glutamicum*: characterization, expression and inactivation of the pyc gene," *Microbiology* 144:915–927, Kluwer Academic/Plenum Publishers, Washington, D.C. (Apr. 1998).

Post, L.E. et al., "Dissection of the Functional Domains of *Escherichia coli* Carbamoyl Phosphate Synthetase by Site–directed Mutagenesis," *J. Biol. Chem.* 265:7742–7747, American Society for Biochemistry and Molecular Biology, Inc., Baltimore, MD (1990).

Reyes, O. et al., "'Integron'–bearing vectors: a method suitable for stable chromosomal integration in highly restrictive Corynebacteria," *Gene* 107:61–68, Elsevier Science Publishers B.V., Amsterdam, Netherlands (1991).

Scrutton, M.C. and Taylor, B.L., "Isolation and Characterization of Pyruvate Carboxylase from *Azotobacter vinelandii* OP," *Arch. Biochem. Biophys.* 164:641–654, Academic Press, New York, NY (1974).

Serwold–Davis, T.M. et al., "Transformation of *Cornyebacterium diphtheriae, Corynebacterium ulcerans, Cornyebacterium glutamicum*, and *Escherichia coli* with the *C. diphtheriae* plasmid pNG2," *Proc. Natl. Acad. Sci. USA* 84:4964–4968, National Academy of Sciences of the USA, Washington, D.C. (1987).

Simon, R. et al., "A Broad Host Range Mobilization System For In Vivo Genetic Engineering: Transposon Mutagenesis in Gram Negative Bacteria," *Bio/Technol.* 1:784–791, Nature Publishing Co., New York (1983).

Sonnen, H. et al., "Characterization of pGA1, a new plasmid from *Cornyebacterium glutamicum* LP–6," *Gene* 107:69–74, Elsevier Science Publishers B.V., Amsterdam, Netherlands (1991).

Toh, H. et al., "Molecular evolution of phosphoenolpyruvate carboxylase," *Plant, Cell and Environ.* 17:31–43, Blackwell Scientific Publications, New York, NY (1994).

Tomioka, N. et al., "Molecular Cloning and Characterization of Ribosomal RNA Genes from a Blue–Green Alga, *Anacystis nidulans*," *Mol. Gen. Genet.* 184:359–363, Springer–Verlag, New York, NY (1981).

Tosaka, O. et al., "The Role of Biotin–Dependent Pyruvate Carboxylase in L–Lysine Production," *Agric. Biol. Chem.* 43(7):1513–1519, Agricultural Chemical Society of Japan, Tokyo, Japan (1979).

Towbin, H. et al., "Electrophoretic transfer of proteins from polyacrylamide gels to nitrocellulose sheets: Procedure and some applications," *Proc. Natl. Acad. Sci. USA* 76:4350–4354, National Academy of Sciences of the USA, Washington, D.C. (1979).

Vallino, J.J. and Stephanopoulos, G., "Metabolic Flux Distributions in *Corynebacterium glutamicum* During Growth and Lysine Overproduction," *Biotechnol. Bioeng.* 41:633–646, Wiley, New York, NY (1993).

Vertès, A.A. et al., "Transposon mutagenesis of cornyeform bacteria," *Mol. Gen. Genet.* 245:397–405, Springer–Verlag, New York, NY (1994).

Wexler, I.D. et al., "Primary amino acid sequence and structure of human pyruvate carboxylase," *Biochim. et Biophys. Acta* 1227:46–52, Elsevier Publishing Co., Amsterdam, Netherlands (1994).

Yoshihama, M. et al., "Cloning Vector System for *Cornyebacterium glutamicum*," *J. Bacteriol.* 162:591–597, American Society for Microbiology, Baltimore, MD (1985).

NCBI Entrez, GenBank Report, Accession No. AF038548, Koffas, M.A.G. et al. (Dec. 1997).

NCBI Entrez, GenBank Report, Accession No. Z83018, Cole, S.T. et al. (Jun. 1998).

NCBI Entrez, GenBank Report, Accession No. Z97025, Kunst, F. et al. (Jun. 1998).

Dialog File 351: Accession No. 12439413, Derwent WPI English language abstract for WO 99/18228.

```
    TGGGGCGGGGTTAGATCCTGGGGGGTTTATTTCATTCAC
    TTTGGCTTGAAGTCGTGCAGGTCAGGGGAGTGTTGCCCGAAAACA
    TTGAGAGGAAAACAAAAACCGATGTTTGATTGGGGGAATCGGGGG
    TTACGATACTAGGACGCAGTGACTGCTATCACCCTTGGCGGTCTC
175 TTGTTGAAAGGAATAATTACTCTAGTGTCGACTCACACATCTTCA
                            M  S  T  H  T  S  S
220 ACGCTTCCAGCATTCAAAAAGATCTTGGTAGCAAACCGCGGCGAA
     T  L  P  A  F  K  K  I  L  V  A  N  R  G  E
265 ATCGCGGTCCGTGCTTTCCGTGCAGCACTCGAAACCGGTGCAGCC
     I  A  V  R  A  F  R  A  A  L  E  T  G  A  A
310 ACGGTAGCTATTTACCCCCGTGAAGATCGGGGATCATTCCACCGC
     T  V  A  I  Y  P  R  E  D  R  G  S  F  H  R
355 TCTTTTGCTTCTGAAGCTGTCCGCATTGGTACCGAAGGCTCACCA
     S  F  A  S  E  A  V  R  I  G  T  E  G  S  P
400 GTCAAGGCGTACCTGGACATCGATGAAATTATCGGTGCAGCTAAA
     V  K  A  Y  L  D  I  D  E  I  I  G  A  A  K
445 AAAGTTAAAGCAGATGCCATTTACCCGGGATACGGCTTCCTGTCT
     K  V  K  A  D  A  I  Y  P  G  Y  G  F  L  S
490 GAAAATGCCCAGCTTGCCCGCGAGTGTGCGGAAAACGGCATTACT
     E  N  A  Q  L  A  R  E  C  A  E  N  G  I  T
535 TTTATTGGCCCCAACCCCAGAGGTTCTTGATCTCACCGGTGATAAG
     F  I  G  P  T  P  E  V  L  D  L  T  G  D  K
580 TCTCGCGCGGTAACCGCCGCGAAGAAGGCTGGTCTGCCAGTTTTG
     S  R  A  V  T  A  A  K  K  A  G  L  P  V  L
625 GCGGAATCCACCCCGAGCAAAAACATCGATGAGATCGTTAAAAGC
     A  E  S  T  P  S  K  N  I  D  E  I  V  K  S
670 GCTGAAGGCCAGACTTACCCCATCTTTGTGAAGGCAGTTGCCGGT
     A  E  G  Q  T  Y  P  I  F  V  K  A  V  A  G
715 GGTGGCGGACGCGGTATGCGTTTTGTTGCTTCACCTGATGAGCTT
     G  G  R  G  M  R  F  V  A  S  P  D  E  L
760 CGCAAATTAGCAACAGAAGCATCTCGTGAAGCTGAAGCGGCTTTC
     R  K  L  A  T  E  A  S  R  E  A  E  A  A  F
805 GGCGATGGCGCGGTATATGTCGAACGTGCTGTGATTAACCCTCAG
     G  D  G  A  V  Y  V  E  R  A  V  I  N  P  Q
850 CATATTGAAGTGCAGATCCTTGGCGATCACACTGGAGAAGTTGTA
     H  I  E  V  Q  I  L  G  D  H  T  G  E  V  V
895 CACCTTTATGAACGTGACTGCTCACTGCAGCGTCGTCACCAAAAA
     H  L  Y  E  R  D  C  S  L  Q  R  R  H  Q  K
940 GTTGTCGAAATTGCGCCAGCACAGCATTTGGATCCAGAACTGCGT
     V  V  E  I  A  P  A  Q  H  L  D  P  E  L  R
```

FIG. 1A

```
 985 GATCGCATTTGTGCGGATGCAGTAAAGTTCTGCCGCTCCATTGGT
      D  R  I  C  A  D  A  V  K  F  C  R  S  I  G
1030 TACCAGGGCGCGGGAACCGTGGAATTCTTGGTCGATGAAAAGGGC
      Y  Q  G  A  G  T  V  E  F  L  V  D  E  K  G
1075 AACCACGTCTTCATCGAAATGAACCCACGTATCCAGGTTGAGCAC
      N  H  V  F  I  E  M  N  P  R  I  Q  V  E  H
1120 ACCGTGACTGAAGAAGTCACCGAGGTGGACCTGGTGAAGGCGCAG
      T  V  T  E  E  V  T  E  V  D  L  V  K  A  Q
1165 ATGCGCTTGGCTGCTGGTGCAACCTTGAAGGAATTGGGTCTGACC
      M  R  L  A  A  G  A  T  L  K  E  L  G  L  T
1210 CAAGATAAGATCAAGACCCACGGTGCAGCACTGCAGTGCCGCATC
      Q  D  K  I  K  T  H  G  A  A  L  Q  C  R  I
1255 ACCACGGAAGATCCAAACAACGGCTTCCGCCCAGATACCGGAACT
      T  T  E  D  P  N  N  G  F  R  P  D  T  G  T
1300 ATCACCGCGTACCGCTCACCAGGCGGAGCTGGCGTTCGTCTTGAC
      I  T  A  Y  R  S  P  G  G  A  G  V  R  L  D
1345 GGTGCAGCTCAGCTCGGTGGCGAAATCACCGCACACTTTGACTCC
      G  A  A  Q  L  G  G  E  I  T  A  H  F  D  S
1390 ATGCTGGTGAAAATGACCTGCCGTGGTTCCGACTTTGAAACTGCT
      M  L  V  K  M  T  C  R  G  S  D  F  E  T  A
1435 GTTGCTCGTGCACAGCGCGCGTTGGCTGAGTTCACCGTGTCTGGT
      V  A  R  A  Q  R  A  L  A  E  F  T  V  S  G
1480 GTTGCAACCAACATTGGTTTCTTGCGTGCGTTGCTGCGGGAAGAG
      V  A  T  N  I  G  F  L  R  A  L  L  R  E  E
1525 GACTTCACTTCCAAGCGCATCGCCACCGGATTCATTGCCGATCAC
      D  F  T  S  K  R  I  A  T  G  F  I  A  D  H
1570 CCGCACCTCCTTCAGGCTCCACCTGCTGATGATGAGCAGGGACGC
      P  H  L  L  Q  A  P  P  A  D  D  E  Q  G  R
1615 ATCCTGGATTACTTGGCAGATGTCACCGTGAACAAGCCTCATGGT
      I  L  D  Y  L  A  D  V  T  V  N  K  P  H  G
1660 GTGCGTCCAAAGGATGTTGCAGCTCCTATCGATAAGCTGCCTAAC
      V  R  P  K  D  V  A  A  P  I  D  K  L  P  N
1705 ATCAAGGATCTGCCACTGCCACGCGGTTCCCGTGACCGCCTGAAG
      I  K  D  L  P  L  P  R  G  S  R  D  R  L  K
1750 CAGCTTGGCCCAGCCGCGTTTGCTCGTGATCTCCGTGAGCAGGAC
      Q  L  G  P  A  A  F  A  R  D  L  R  E  Q  D
1795 GCACTGGCAGTTACTGATACCACCTTCCGCGATGCACACCAGTCT
      A  L  A  V  T  D  T  T  F  R  D  A  H  Q  S
```

FIG. 1B

```
1840 TTGCTTGCGACCCGAGTCCGCTCATTCGCACTGAAGCCTGCGGCA
      L  L  A  T  R  V  R  S  F  A  L  K  P  A  A
1885 GAGGCCGTCGCAAAGCTGACTCCTGAGCTTTTGTCCGTGGAGGCC
      E  A  V  A  K  L  T  P  E  L  L  S  V  E  A
1930 TGGGGCGGCGCGACCTACGATGTGGCGATGCGTTTCCTCTTTGAG
      W  G  G  A  T  Y  D  V  A  M  R  F  L  F  E
1975 GATCCGTGGGACAGGCTCGACGAGCTGCGCGAGGCGATGCCGAAT
      D  P  W  D  R  L  D  E  L  R  E  A  M  P  N
2020 GTAAACATTCAGATGCTGCTTCGCGGCCGCAACACCGTGGGATAC
      V  N  I  Q  M  L  L  R  G  R  N  T  V  G  Y
2065 ACCCCGTACCCAGACTCCGTCTGCCGCGCGTTTGTTAAGGAAGCT
      T  P  Y  P  D  S  V  C  R  A  F  V  K  E  A
2110 GCCAGCTCCGGCGTGGACATCTTCCGCATCTTCGACGCGCTTAAC
      A  S  S  G  V  D  I  F  R  I  F  D  A  L  N
2155 GACGTCTCCCAGATGCGTCCAGCAATCGACGCAGTCCTGGAGACC
      D  V  S  Q  M  R  P  A  I  D  A  V  L  E  T
2200 AACACCGCGGTAGCCGAGGTGGCTATGGCTTATTCTGGTGATCTC
      N  T  A  V  A  E  V  A  M  A  Y  S  G  D  L
2245 TCTGATCCAAATGAAAAGCTCTACACCCTGGATTACTACCTAAAG
      S  D  P  N  E  K  L  Y  T  L  D  Y  Y  L  K
2290 ATGGCAGAGGAGATCGTCAAGTCTGGCGCTCACATCTTGGCCATT
      M  A  E  E  I  V  K  S  G  A  H  I  L  A  I
2335 AAGGATATGGCTGGTCTGCTTCGCCCAGCTGCGGTAACCAAGCTG
      K  D  M  A  G  L  L  R  P  A  A  V  T  K  L
2380 GTCACCGCACTGCGCCGTGAATTCGATCTGCCAGTGCACGTGCAC
      V  T  A  L  R  R  E  F  D  L  P  V  H  V  H
2425 ACCCACGACACTGCGGGTGGCCAGCTGGCAACCTACTTTGCTGCA
      T  H  D  T  A  G  G  Q  L  A  T  Y  F  A  A
2470 GCTCAAGCTGGTGCAGATGCTGTTGACGGTGCTTCCGCACCACTG
      A  Q  A  G  A  D  A  V  D  G  A  S  A  P  L
2515 TCTGGCACCACCTCCCAGCCATCCCTGTCTGCCATTGTTGCTGCA
      S  G  T  T  S  Q  P  S  L  S  A  I  V  A  A
2560 TTCGCGCACACCCGTCGCGATACCGGTTTGAGCCTCGAGGCTGTT
      F  A  H  T  R  R  D  T  G  L  S  L  E  A  V
2605 TCTGACCTCGAGCCGTACTGGGAAGCAGTGCGCGGACTGTACCTG
      S  D  L  E  P  Y  W  E  A  V  R  G  L  Y  L
2650 CCATTTGAGTCTGGAACCCCAGGCCCAACCGGTCGCGTCTACCGC
      P  F  E  S  G  T  P  G  P  T  G  R  V  Y  R
2695 CACGAAATCCCAGGCGGACAGTTGTCCAACCTGCGTGCACAGGCC
      H  E  I  P  G  G  Q  L  S  N  L  R  A  Q  A
```

FIG. 1C

SEQUENCE LISTING

<160> NUMBER OF SEQ ID NOS: 39

<210> SEQ ID NO 1
<211> LENGTH: 3621
<212> TYPE: DNA
<213> ORGANISM: Corynebacterium glutamicum
<220> FEATURE:
<221> NAME/KEY: CDS
<222> LOCATION: (199)..(3621)

<400> SEQUENCE: 1

```
tggggcgggg ttagatcctg gggggtttat ttcattcact ttggcttgaa gtcgtgcagg      60 tcagggagt gttgcccgaa acattgaga ggaaaacaaa aaccgatgtt tgattggggg      120
aatcgggggt tacgatacta ggacgcagtg actgctatca cccttggcgg tctcttgttg    180
aaaggaataa ttactcta gtg tcg act cac aca tct tca acg ctt cca gca      231
                    Met Ser Thr His Thr Ser Ser Thr Leu Pro Ala
                     1               5                  10 ttc aaa aag atc ttg gta gca aac cgc ggc gaa atc gcg gtc cgt gct      279
Phe Lys Lys Ile Leu Val Ala Asn Arg Gly Glu Ile Ala Val Arg Ala
            15                  20                  25 ttc cgt gca gca ctc gaa acc ggt gca gcc acg gta gct att tac ccc      327
Phe Arg Ala Ala Leu Glu Thr Gly Ala Ala Thr Val Ala Ile Tyr Pro
        30                  35                  40 cgt gaa gat cgg gga tca ttc cac cgc tct ttt gct tct gaa gct gtc      375
Arg Glu Asp Arg Gly Ser Phe His Arg Ser Phe Ala Ser Glu Ala Val
    45                  50                  55 cgc att ggt acc gaa ggc tca cca gtc aag gcg tac ctg gac atc gat      423
Arg Ile Gly Thr Glu Gly Ser Pro Val Lys Ala Tyr Leu Asp Ile Asp
60                  65                  70                  75 gaa att atc ggt gca gct aaa aaa gtt aaa gca gat gcc att tac ccg      471
Glu Ile Ile Gly Ala Ala Lys Lys Val Lys Ala Asp Ala Ile Tyr Pro
                80                  85                  90 gga tac ggc ttc ctg tct gaa aat gcc cag ctt gcc cgc gag tgt gcg      519
Gly Tyr Gly Phe Leu Ser Glu Asn Ala Gln Leu Ala Arg Glu Cys Ala
            95                 100                 105 gaa aac ggc att act ttt att ggc cca acc cca gag gtt ctt gat ctc      567
Glu Asn Gly Ile Thr Phe Ile Gly Pro Thr Pro Glu Val Leu Asp Leu
        110                 115                 120 acc ggt gat aag tct cgc gcg gta acc gcc gcg aag aag gct ggt ctg      615
Thr Gly Asp Lys Ser Arg Ala Val Thr Ala Ala Lys Lys Ala Gly Leu
    125                 130                 135 cca gtt ttg gcg gaa tcc acc ccg agc aaa aac atc gat gag atc gtt      663
Pro Val Leu Ala Glu Ser Thr Pro Ser Lys Asn Ile Asp Glu Ile Val
140                 145                 150                 155 aaa agc gct gaa ggc cag act tac ccc atc ttt gtg aag gca gtt gcc      711
Lys Ser Ala Glu Gly Gln Thr Tyr Pro Ile Phe Val Lys Ala Val Ala
                160                 165                 170 ggt ggt ggc gga cgc ggt atg cgt ttt gtt gct tca cct gat gag ctt      759
Gly Gly Gly Gly Arg Gly Met Arg Phe Val Ala Ser Pro Asp Glu Leu
            175                 180                 185 cgc aaa tta gca aca gaa gca tct cgt gaa gct gaa gcg gct ttc ggc      807
Arg Lys Leu Ala Thr Glu Ala Ser Arg Glu Ala Glu Ala Ala Phe Gly
        190                 195                 200
```

-continued

| | | |
|---|---|---|
| gat ggc gcg gta tat gtc gaa cgt gct gtg att aac cct cag cat att<br>Asp Gly Ala Val Tyr Val Glu Arg Ala Val Ile Asn Pro Gln His Ile<br>205                             210                           215 | 855 |
| gaa gtg cag atc ctt ggc gat cac act gga gaa gtt gta cac ctt tat<br>Glu Val Gln Ile Leu Gly Asp His Thr Gly Glu Val Val His Leu Tyr<br>220                           225                       230                   235 | 903 |
| gaa cgt gac tgc tca ctg cag cgt cgt cac caa aaa gtt gtc gaa att<br>Glu Arg Asp Cys Ser Leu Gln Arg Arg His Gln Lys Val Val Glu Ile<br>                      240                       245                   250 | 951 |
| gcg cca gca cag cat ttg gat cca gaa ctg cgt gat cgc att tgt gcg<br>Ala Pro Ala Gln His Leu Asp Pro Glu Leu Arg Asp Arg Ile Cys Ala<br>255                             260                       265 | 999 |
| gat gca gta aag ttc tgc cgc tcc att ggt tac cag ggc gcg gga acc<br>Asp Ala Val Lys Phe Cys Arg Ser Ile Gly Tyr Gln Gly Ala Gly Thr<br>      270                     275                       280 | 1047 |
| gtg gaa ttc ttg gtc gat gaa aag ggc aac cac gtc ttc atc gaa atg<br>Val Glu Phe Leu Val Asp Glu Lys Gly Asn His Val Phe Ile Glu Met<br>285                           290                       295 | 1095 |
| aac cca cgt atc cag gtt gag cac acc gtg act gaa gaa gtc acc gag<br>Asn Pro Arg Ile Gln Val Glu His Thr Val Thr Glu Glu Val Thr Glu<br>300                             305                       310                   315 | 1143 |
| gtg gac ctg gtg aag gcg cag atg cgc ttg gct gct ggt gca acc ttg<br>Val Asp Leu Val Lys Ala Gln Met Arg Leu Ala Ala Gly Ala Thr Leu<br>                   320                       325                       330 | 1191 |
| aag gaa ttg ggt ctg acc caa gat aag atc aag acc cac ggt gca gca<br>Lys Glu Leu Gly Leu Thr Gln Asp Lys Ile Lys Thr His Gly Ala Ala<br>             335                       340                       345 | 1239 |
| ctg cag tgc cgc atc acc acg gaa gat cca aac aac ggc ttc cgc cca<br>Leu Gln Cys Arg Ile Thr Thr Glu Asp Pro Asn Asn Gly Phe Arg Pro<br>         350                     355                       360 | 1287 |
| gat acc gga act atc acc gcg tac cgc tca cca ggc gga gct ggc gtt<br>Asp Thr Gly Thr Ile Thr Ala Tyr Arg Ser Pro Gly Gly Ala Gly Val<br>365                             370                       375 | 1335 |
| cgt ctt gac ggt gca gct cag ctc ggt ggc gaa atc acc gca cac ttt<br>Arg Leu Asp Gly Ala Ala Gln Leu Gly Gly Glu Ile Thr Ala His Phe<br>380                             385                       390                   395 | 1383 |
| gac tcc atg ctg gtg aaa atg acc tgc cgt ggt tcc gac ttt gaa act<br>Asp Ser Met Leu Val Lys Met Thr Cys Arg Gly Ser Asp Phe Glu Thr<br>                   400                       405                       410 | 1431 |
| gct gtt gct cgt gca cag cgc gcg ttg gct gag ttc acc gtg tct ggt<br>Ala Val Ala Arg Ala Gln Arg Ala Leu Ala Glu Phe Thr Val Ser Gly<br>             415                       420                       425 | 1479 |
| gtt gca acc aac att ggt ttc ttg cgt gcg ttg ctg cgg gaa gag gac<br>Val Ala Thr Asn Ile Gly Phe Leu Arg Ala Leu Leu Arg Glu Glu Asp<br>430                             435                       440 | 1527 |
| ttc act tcc aag cgc atc gcc acc gga ttc att gcc gat cac ccg cac<br>Phe Thr Ser Lys Arg Ile Ala Thr Gly Phe Ile Ala Asp His Pro His<br>445                             450                       455 | 1575 |
| ctc ctt cag gct cca cct gct gat gat gag cag gga cgc atc ctg gat<br>Leu Leu Gln Ala Pro Pro Ala Asp Asp Glu Gln Gly Arg Ile Leu Asp<br>460                             465                       470                   475 | 1623 |
| tac ttg gca gat gtc acc gtg aac aag cct cat ggt gtg cgt cca aag<br>Tyr Leu Ala Asp Val Thr Val Asn Lys Pro His Gly Val Arg Pro Lys<br>                   480                       485                   490 | 1671 |
| gat gtt gca gct cct atc gat aag ctg cct aac atc aag gat ctg cca<br>Asp Val Ala Ala Pro Ile Asp Lys Leu Pro Asn Ile Lys Asp Leu Pro<br>             495                       500                       505 | 1719 |
| ctg cca cgc ggt tcc cgt gac cgc ctg aag cag ctt ggc cca gcc gcg<br>Leu Pro Arg Gly Ser Arg Asp Arg Leu Lys Gln Leu Gly Pro Ala Ala<br>         510                     515                       520 | 1767 |

-continued

| | |
|---|---|
| ttt gct cgt gat ctc cgt gag cag gac gca ctg gca gtt act gat acc<br>Phe Ala Arg Asp Leu Arg Glu Gln Asp Ala Leu Ala Val Thr Asp Thr<br>525                      530                    535 | 1815 |
| acc ttc cgc gat gca cac cag tct ttg ctt gcg acc cga gtc cgc tca<br>Thr Phe Arg Asp Ala His Gln Ser Leu Leu Ala Thr Arg Val Arg Ser<br>540                      545                    550                    555 | 1863 |
| ttc gca ctg aag cct gcg gca gag gcc gtc gca aag ctg act cct gag<br>Phe Ala Leu Lys Pro Ala Ala Glu Ala Val Ala Lys Leu Thr Pro Glu<br>                    560                    565                    570 | 1911 |
| ctt ttg tcc gtg gag gcc tgg ggc ggc gcg acc tac gat gtg gcg atg<br>Leu Leu Ser Val Glu Ala Trp Gly Gly Ala Thr Tyr Asp Val Ala Met<br>                  575                    580                    585 | 1959 |
| cgt ttc ctc ttt gag gat ccg tgg gac agg ctc gac gag ctg cgc gag<br>Arg Phe Leu Phe Glu Asp Pro Trp Asp Arg Leu Asp Glu Leu Arg Glu<br>590                      595                    600 | 2007 |
| gcg atg ccg aat gta aac att cag atg ctg ctt cgc ggc cgc aac acc<br>Ala Met Pro Asn Val Asn Ile Gln Met Leu Leu Arg Gly Arg Asn Thr<br>            605                    610                    615 | 2055 |
| gtg gga tac acc ccg tac cca gac tcc gtc tgc cgc gcg ttt gtt aag<br>Val Gly Tyr Thr Pro Tyr Pro Asp Ser Val Cys Arg Ala Phe Val Lys<br>620                      625                    630                    635 | 2103 |
| gaa gct gcc agc tcc ggc gtg gac atc ttc cgc atc ttc gac gcg ctt<br>Glu Ala Ala Ser Ser Gly Val Asp Ile Phe Arg Ile Phe Asp Ala Leu<br>                    640                    645                    650 | 2151 |
| aac gac gtc tcc cag atg cgt cca gca atc gac gca gtc ctg gag acc<br>Asn Asp Val Ser Gln Met Arg Pro Ala Ile Asp Ala Val Leu Glu Thr<br>                  655                    660                    665 | 2199 |
| aac acc gcg gta gcc gag gtg gct atg gct tat tct ggt gat ctc tct<br>Asn Thr Ala Val Ala Glu Val Ala Met Ala Tyr Ser Gly Asp Leu Ser<br>670                      675                    680 | 2247 |
| gat cca aat gaa aag ctc tac acc ctg gat tac tac cta aag atg gca<br>Asp Pro Asn Glu Lys Leu Tyr Thr Leu Asp Tyr Tyr Leu Lys Met Ala<br>            685                    690                    695 | 2295 |
| gag gag atc gtc aag tct ggc gct cac atc ttg gcc att aag gat atg<br>Glu Glu Ile Val Lys Ser Gly Ala His Ile Leu Ala Ile Lys Asp Met<br>700                      705                    710                    715 | 2343 |
| gct ggt ctg ctt cgc cca gct gcg gta acc aag ctg gtc acc gca ctg<br>Ala Gly Leu Leu Arg Pro Ala Ala Val Thr Lys Leu Val Thr Ala Leu<br>                    720                    725                    730 | 2391 |
| cgc cgt gaa ttc gat ctg cca gtg cac gtg cac acc cac gac act gcg<br>Arg Arg Glu Phe Asp Leu Pro Val His Val His Thr His Asp Thr Ala<br>                  735                    740                    745 | 2439 |
| ggt ggc cag ctg gca acc tac ttt gct gca gct caa gct ggt gca gat<br>Gly Gly Gln Leu Ala Thr Tyr Phe Ala Ala Ala Gln Ala Gly Ala Asp<br>750                      755                    760 | 2487 |
| gct gtt gac ggt gct tcc gca cca ctg tct ggc acc acc tcc cag cca<br>Ala Val Asp Gly Ala Ser Ala Pro Leu Ser Gly Thr Thr Ser Gln Pro<br>765                      770                    775 | 2535 |
| tcc ctg tct gcc att gtt gct gca ttc gcg cac acc cgt cgc gat acc<br>Ser Leu Ser Ala Ile Val Ala Ala Phe Ala His Thr Arg Arg Asp Thr<br>780                      785                    790                    795 | 2583 |
| ggt ttg agc ctc gag gct gtt tct gac ctc gag ccg tac tgg gaa gca<br>Gly Leu Ser Leu Glu Ala Val Ser Asp Leu Glu Pro Tyr Trp Glu Ala<br>                  800                    805                    810 | 2631 |
| gtg cgc gga ctg tac ctg cca ttt gag tct gga acc cca ggc cca acc<br>Val Arg Gly Leu Tyr Leu Pro Phe Glu Ser Gly Thr Pro Gly Pro Thr<br>                  815                    820                    825 | 2679 |
| ggt cgc gtc tac cgc cac gaa atc cca ggc gga cag ttg tcc aac ctg<br>Gly Arg Val Tyr Arg His Glu Ile Pro Gly Gly Gln Leu Ser Asn Leu | 2727 |

-continued

| | |
|---|---|
| cgt gca cag gcc acc gca ctg ggc ctt gcg gat cgt ttc gaa ctc atc<br>Arg Ala Gln Ala Thr Ala Leu Gly Leu Ala Asp Arg Phe Glu Leu Ile<br>845                850                855 | 2775 |
| gaa gac aac tac gca gcc gtt aat gag atg ctg gga cgc cca acc aag<br>Glu Asp Asn Tyr Ala Ala Val Asn Glu Met Leu Gly Arg Pro Thr Lys<br>860                865              870              875 | 2823 |
| gtc acc cca tcc tcc aag gtt gtt ggc gac ctc gca ctc cac ctc gtt<br>Val Thr Pro Ser Ser Lys Val Val Gly Asp Leu Ala Leu His Leu Val<br>              880              885              890 | 2871 |
| ggt gcg ggt gtg gat cca gca gac ttt gct gcc gat cca caa aag tac<br>Gly Ala Gly Val Asp Pro Ala Asp Phe Ala Ala Asp Pro Gln Lys Tyr<br>        895                900              905 | 2919 |
| gac atc cca gac tct gtc atc gcg ttc ctg cgc ggc gag ctt ggt aac<br>Asp Ile Pro Asp Ser Val Ile Ala Phe Leu Arg Gly Glu Leu Gly Asn<br>910                915              920 | 2967 |
| cct cca ggt ggc tgg cca gag cca ctg cgc acc cgc gca ctg gaa ggc<br>Pro Pro Gly Gly Trp Pro Glu Pro Leu Arg Thr Arg Ala Leu Glu Gly<br>925                930              935 | 3015 |
| cgc tcc gaa ggc aag gca cct ctg acg gaa gtt cct gag gaa gag cag<br>Arg Ser Glu Gly Lys Ala Pro Leu Thr Glu Val Pro Glu Glu Glu Gln<br>940                945              950              955 | 3063 |
| gcg cac ctc gac gct gat gat tcc aag gaa cgt cgc aat agc ctc aac<br>Ala His Leu Asp Ala Asp Asp Ser Lys Glu Arg Arg Asn Ser Leu Asn<br>              960              965              970 | 3111 |
| cgc ctg ctg ttc ccg aag cca acc gaa gag ttc ctc gag cac cgt cgc<br>Arg Leu Leu Phe Pro Lys Pro Thr Glu Glu Phe Leu Glu His Arg Arg<br>        975                980              985 | 3159 |
| cgc ttc ggc aac acc tct gcg ctg gat gat cgt gaa ttc ttc tac ggc<br>Arg Phe Gly Asn Thr Ser Ala Leu Asp Asp Arg Glu Phe Phe Tyr Gly<br>990                995              1000 | 3207 |
| ctg gtc gaa ggc cgc gag act ttg atc cgc ctg cca gat gtg cgc acc<br>Leu Val Glu Gly Arg Glu Thr Leu Ile Arg Leu Pro Asp Val Arg Thr<br>1005               1010             1015 | 3255 |
| cca ctg ctt gtt cgc ctg gat gcg atc tct gag cca gac gat aag ggt<br>Pro Leu Leu Val Arg Leu Asp Ala Ile Ser Glu Pro Asp Asp Lys Gly<br>1020               1025             1030             1035 | 3303 |
| atg cgc aat gtt gtg gcc aac gtc aac ggc cag atc cgc cca atg cgt<br>Met Arg Asn Val Val Ala Asn Val Asn Gly Gln Ile Arg Pro Met Arg<br>           1040             1045             1050 | 3351 |
| gtg cgt gac cgc tcc gtt gag tct gtc acc gca acc gca gaa aag gca<br>Val Arg Asp Arg Ser Val Glu Ser Val Thr Ala Thr Ala Glu Lys Ala<br>1055               1060             1065 | 3399 |
| gat tcc tcc aac aag ggc cat gtt gct gca cca ttc gct ggt gtt gtc<br>Asp Ser Ser Asn Lys Gly His Val Ala Ala Pro Phe Ala Gly Val Val<br>1070               1075             1080 | 3447 |
| acc gtg act gtt gct gaa ggt gat gag gtc aag gct gga gat gca gtc<br>Thr Val Thr Val Ala Glu Gly Asp Glu Val Lys Ala Gly Asp Ala Val<br>1085               1090             1095 | 3495 |
| gca atc atc gag gct atg aag atg gaa gca aca atc act gct tct gtt<br>Ala Ile Ile Glu Ala Met Lys Met Glu Ala Thr Ile Thr Ala Ser Val<br>1100               1105             1110             1115 | 3543 |
| gac ggc aaa atc gat cgc gtt gtg gtt cct gct gca acg aag gtg gaa<br>Asp Gly Lys Ile Asp Arg Val Val Val Pro Ala Ala Thr Lys Val Glu<br>           1120             1125             1130 | 3591 |
| ggt ggc gac ttg atc gtc gtc gtt tcc taa<br>Gly Gly Asp Leu Ile Val Val Val Ser<br>1135               1140 | 3621 |

<210> SEQ ID NO 2
<211> LENGTH: 1140
<212> TYPE: PRT
<213> ORGANISM: Corynebacterium glutamicum

<400> SEQUENCE: 2

```
Met Ser Thr His Thr Ser Ser Thr Leu Pro Ala Phe Lys Lys Ile Leu
 1               5                  10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380
```

```
Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
            405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
            450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
            485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
            565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
            610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
            645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
            725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
            770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
```

-continued

```
                805                 810                 815
Leu Pro Phe Glu Ser Gly Thr Pro Gly Pro Thr Gly Arg Val Tyr Arg
            820                 825                 830
His Glu Ile Pro Gly Gly Gln Leu Ser Asn Leu Arg Ala Gln Ala Thr
            835                 840                 845
Ala Leu Gly Leu Ala Asp Arg Phe Glu Leu Ile Glu Asp Asn Tyr Ala
            850                 855                 860
Ala Val Asn Glu Met Leu Gly Arg Pro Thr Lys Val Thr Pro Ser Ser
865                 870                 875                 880
Lys Val Val Gly Asp Leu Ala Leu His Leu Val Gly Ala Gly Val Asp
                885                 890                 895
Pro Ala Asp Phe Ala Ala Asp Pro Gln Lys Tyr Asp Ile Pro Asp Ser
                900                 905                 910
Val Ile Ala Phe Leu Arg Gly Glu Leu Gly Asn Pro Pro Gly Gly Trp
            915                 920                 925
Pro Glu Pro Leu Arg Thr Arg Ala Leu Glu Gly Arg Ser Glu Gly Lys
            930                 935                 940
Ala Pro Leu Thr Glu Val Pro Glu Glu Gln Ala His Leu Asp Ala
945                 950                 955                 960
Asp Asp Ser Lys Glu Arg Arg Asn Ser Leu Asn Arg Leu Leu Phe Pro
                965                 970                 975
Lys Pro Thr Glu Glu Phe Leu Glu His Arg Arg Arg Phe Gly Asn Thr
            980                 985                 990
Ser Ala Leu Asp Asp Arg Glu Phe Phe Tyr Gly Leu Val Glu Gly Arg
            995                 1000                1005
Glu Thr Leu Ile Arg Leu Pro Asp Val Arg Thr Pro Leu Leu Val Arg
    1010                1015                1020
Leu Asp Ala Ile Ser Glu Pro Asp Asp Lys Gly Met Arg Asn Val Val
1025                1030                1035                1040
Ala Asn Val Asn Gly Gln Ile Arg Pro Met Arg Val Arg Asp Arg Ser
                1045                1050                1055
Val Glu Ser Val Thr Ala Thr Ala Glu Lys Ala Asp Ser Ser Asn Lys
            1060                1065                1070
Gly His Val Ala Ala Pro Phe Ala Gly Val Val Thr Val Thr Val Ala
            1075                1080                1085
Glu Gly Asp Glu Val Lys Ala Gly Asp Ala Val Ala Ile Ile Glu Ala
    1090                1095                1100
Met Lys Met Glu Ala Thr Ile Thr Ala Ser Val Asp Gly Lys Ile Asp
1105                1110                1115                1120
Arg Val Val Pro Ala Ala Thr Lys Val Glu Gly Gly Asp Leu Ile
                1125                1130                1135
Val Val Val Ser
        1140

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Forward DNA
      Primer

<400> SEQUENCE: 3
gtcttcatcg agatgaatcc gcg                                              23
```

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Reverse DNA
      Primer

<400> SEQUENCE: 4
cgcagcgcca catcgtaagt cgc                                              23

<210> SEQ ID NO 5
<211> LENGTH: 8
<212> TYPE: PRT
<213> ORGANISM: Caenorhabditis elegans

<400> SEQUENCE: 5

Tyr Phe Ile Glu Val Asn Ala Arg
  1               5

<210> SEQ ID NO 6
<211> LENGTH: 7
<212> TYPE: PRT
<213> ORGANISM: Caenorhabditis elegans

<400> SEQUENCE: 6

Ala Thr Phe Asp Val Ser Met
  1               5

<210> SEQ ID NO 7
<211> LENGTH: 8
<212> TYPE: PRT
<213> ORGANISM: Aedes aegypti

<400> SEQUENCE: 7

Tyr Phe Ile Glu Val Asn Ala Arg
  1               5

<210> SEQ ID NO 8
<211> LENGTH: 7
<212> TYPE: PRT
<213> ORGANISM: Aedes aegypti

<400> SEQUENCE: 8

Ala Thr Phe Asp Val Ala Leu
  1               5

<210> SEQ ID NO 9
<211> LENGTH: 8
<212> TYPE: PRT
<213> ORGANISM: Mycobacterium tuberculosis

<400> SEQUENCE: 9

Val Phe Ile Glu Met Asn Pro Arg
  1               5

<210> SEQ ID NO 10
<211> LENGTH: 7
<212> TYPE: PRT
<213> ORGANISM: Mycobacterium tuberculosis

<400> SEQUENCE: 10

Ala Thr Tyr Asp Val Ala Leu
  1               5
```

```
<210> SEQ ID NO 11
<211> LENGTH: 8
<212> TYPE: PRT
<213> ORGANISM: Bacillus stearothermophilus

<400> SEQUENCE: 11

Tyr Phe Ile Glu Val Asn Pro Arg
  1               5

<210> SEQ ID NO 12
<211> LENGTH: 7
<212> TYPE: PRT
<213> ORGANISM: Bacillus stearothermophilus

<400> SEQUENCE: 12

Ala Thr Phe Asp Val Ala Tyr
  1               5

<210> SEQ ID NO 13
<211> LENGTH: 8
<212> TYPE: PRT
<213> ORGANISM: Pichia pastoris

<400> SEQUENCE: 13

Tyr Phe Ile Glu Ile Asn Pro Arg
  1               5

<210> SEQ ID NO 14
<211> LENGTH: 7
<212> TYPE: PRT
<213> ORGANISM: Pichia pastoris

<400> SEQUENCE: 14

Ala Thr Phe Asp Val Ser Met
  1               5

<210> SEQ ID NO 15
<211> LENGTH: 8
<212> TYPE: PRT
<213> ORGANISM: Mus musculus

<400> SEQUENCE: 15

Tyr Phe Ile Glu Val Asn Ser Arg
  1               5

<210> SEQ ID NO 16
<211> LENGTH: 7
<212> TYPE: PRT
<213> ORGANISM: Mus musculus

<400> SEQUENCE: 16

Ala Thr Phe Asp Val Ala Met
  1               5

<210> SEQ ID NO 17
<211> LENGTH: 8
<212> TYPE: PRT
<213> ORGANISM: Rattus norvegicus

<400> SEQUENCE: 17

Tyr Phe Ile Glu Val Asn Ser Arg
  1               5

<210> SEQ ID NO 18
<211> LENGTH: 7
```

```
<212> TYPE: PRT
<213> ORGANISM: Rattus norvegicus

<400> SEQUENCE: 18

Ala Thr Phe Asp Val Ala Met
 1               5

<210> SEQ ID NO 19
<211> LENGTH: 8
<212> TYPE: PRT
<213> ORGANISM: Saccharomyces cerevisiae 1

<400> SEQUENCE: 19

Tyr Phe Ile Glu Ile Asn Pro Arg
 1               5

<210> SEQ ID NO 20
<211> LENGTH: 7
<212> TYPE: PRT
<213> ORGANISM: Saccharomyces cerevisiae 1

<400> SEQUENCE: 20

Ala Thr Phe Asp Val Ala Met
 1               5

<210> SEQ ID NO 21
<211> LENGTH: 8
<212> TYPE: PRT
<213> ORGANISM: Saccharomyces cerevisiae 2

<400> SEQUENCE: 21

Tyr Phe Ile Glu Ile Asn Pro Arg
 1               5

<210> SEQ ID NO 22
<211> LENGTH: 7
<212> TYPE: PRT
<213> ORGANISM: Saccharomyces cerevisiae 2

<400> SEQUENCE: 22

Ala Thr Phe Asp Val Ala Met
 1               5

<210> SEQ ID NO 23
<211> LENGTH: 8
<212> TYPE: PRT
<213> ORGANISM: Rhizobium etli

<400> SEQUENCE: 23

Tyr Phe Ile Glu Val Asn Pro Arg
 1               5

<210> SEQ ID NO 24
<211> LENGTH: 7
<212> TYPE: PRT
<213> ORGANISM: Rhizobium etli

<400> SEQUENCE: 24

Ala Thr Phe Asp Val Ser Met
 1               5

<210> SEQ ID NO 25
<211> LENGTH: 8
<212> TYPE: PRT
<213> ORGANISM: Homo sapiens
```

```
<400> SEQUENCE: 25

Tyr Phe Ile Glu Val Asn Ser Arg
  1               5

<210> SEQ ID NO 26
<211> LENGTH: 7
<212> TYPE: PRT
<213> ORGANISM: Homo sapiens

<400> SEQUENCE: 26

Ala Thr Phe Asp Val Ala Met
  1               5

<210> SEQ ID NO 27
<211> LENGTH: 8
<212> TYPE: PRT
<213> ORGANISM: Schizosaccharomyces pombe

<400> SEQUENCE: 27

Tyr Phe Ile Glu Ile Asn Pro Arg
  1               5

<210> SEQ ID NO 28
<211> LENGTH: 7
<212> TYPE: PRT
<213> ORGANISM: Schizosaccharomyces pombe

<400> SEQUENCE: 28

Ala Thr Phe Asp Val Ser Met
  1               5

<210> SEQ ID NO 29
<211> LENGTH: 9
<212> TYPE: PRT
<213> ORGANISM: Corynebacterium glutamicum

<400> SEQUENCE: 29

Phe Leu Phe Glu Asp Pro Trp Asp Arg
  1               5

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 30
ttcaccaggt ccacctcg                                                    18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 31
cgtcgcaaag ctgactcc                                                    18

<210> SEQ ID NO 32
<211> LENGTH: 22
<212> TYPE: DNA
<213> ORGANISM: Artificial Sequence
```

```
<220> FEATURE:
<223> OTHER INFORMATION: Description of Artificial Sequence: DNA Primer

<400> SEQUENCE: 32
gatgcttctg ttgctaattt gc                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: DNA Primer

<400> SEQUENCE: 33
ggccattaag gatatggctg                                                 20

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: DNA Primer

<400> SEQUENCE: 34
gcggtggaat gatccccga                                                  19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 35
accgcactgg gccttgcg                                                   18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 36
tcgccgcttc ggcaacac                                                   18

<210> SEQ ID NO 37
<211> LENGTH: 6
<212> TYPE: PRT
<213> ORGANISM: Corynebacterium glutamicum

<400> SEQUENCE: 37

Gly Gly Gly Gly Arg Gly
 1               5

<210> SEQ ID NO 38
<211> LENGTH: 6
<212> TYPE: PRT
<213> ORGANISM: Corynebacterium glutamicum
<220> FEATURE:
<221> NAME/KEY: MISC_FEATURE
<222> LOCATION: (5)..(5)
<223> OTHER INFORMATION: May be Arg or Lys

<400> SEQUENCE: 38

Gly Gly Gly Gly Xaa Gly
```

```
<210> SEQ ID NO 39
<211> LENGTH: 4
<212> TYPE: PRT
<213> ORGANISM: Unknown
<220> FEATURE:
<223> OTHER INFORMATION: Putative biotin-binding site

<400> SEQUENCE: 39

Ala Met Lys Met
  1
```

PYRUVATE CARBOXYLASE FROM CORYNEBACTERIUM GLUTAMICUM

This application is a Divisional of U.S. application Ser. No. 09/677,575, filed Oct. 3, 2000 now U.S. Pat. No. 6,403,351, issued Jun. 11, 2002, which is a Divisional of U.S. application Ser. No. 09/220,081 filed Dec. 23, 1998, now U.S. Pat. No. 6,171,833, issued Jan. 9, 2001.

STATEMENT OF GOVERNMENT RIGHTS IN THE INVENTION

Part of the work performed during development of this invention utilized U.S. Government funds. The U.S. Government has certain rights in this invention.

BACKGROUND OF THE INVENTION

1. Field of the Invention

The present invention relates to a *Corynebacterium glutamicum* pyruvate carboxylase protein and to polynucleotides encoding this protein.

2. Background Information

Pyruvate carboxylate is an important anaplerotic enzyme replenishing oxaloacetate consumed for biosynthesis during growth, or lysine and glutamic acid production in industrial fermentations.

The two-step reaction mechanism catalyzed by pyruvate carboxylase is shown below:

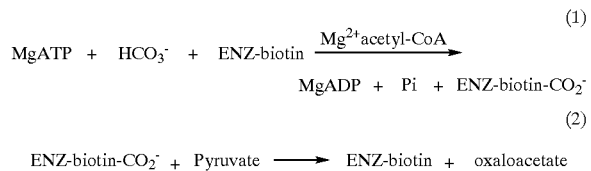

In reaction (1) the ATP-dependent biotin carboxylase domain carboxylates a biotin prosthetic group linked to a specific lysine residue in the biotin-carboxyl-carrier protein (BCCP) domain. Acetyl-coenzyme A activates reaction (1) by increasing the rate of bicarbonate-dependent ATP cleavage. In reaction (2), the BCCP domain donates the $CO_2$ to pyruvate in a reaction catalyzed by the transcarboxylase domain (Attwood, P. V., *Int. J. Biochem. Cell. Biol.* 27:231–249 (1995)).

Pruvate carboxylase genes have been cloned and sequenced from: *Rhizobium etli* (Dunn, M. F., et al., *J. Bacteriol.* 178:5960–5970 (1996)), *Bacillus stearothermophilus* (Kondo, H., et al., *Gene* 191:47–50 (1997), *Bacillus subtillis* (Genbank accession no. Z97025), *Mycobacterium tuberculosis* (Genbank accession no. Z83018), and *Methanobacterium thermoautotrophicum* (Mukhopadhyay, B., *J. Biol. Chem.* 273:5155–5166 (1998). Pyruvate carboxylase activity has been measured previously in *Brevibacterium lactofermentum* (Tosaka, O., et al., *Agric. Biol. Chem.* 43:1513–1519 (1979)) and *Corynebacterium glutamicum* (Peters-Wendisch, P. G., et al., *Microbiology* 143:1095–1103 (1997)).

Previous research has indicated that the yield and productivity of the aspartate family of amino acids depends critically on the carbon flux through anaplerotic pathways (Vallino, J. J., & Stephanopoulos, G., *Biotechnol. Bioeng.* 41:633–646 (1993)). On the basis of the metabolite balances, it can be shown that the rate of lysine production is less than or equal to the rate of oxaloacetate synthesis via the anaplerotic pathways.

SUMMARY OF THE INVENTION

The present invention provides isolated nucleic acid molecules comprising a polynucleotide encoding a pyruvate carboxylase polypeptide having the amino acid sequence in FIGS. 1A–C (SEQ ID NO:2) or the amino acid sequence encoded by the clone deposited in a bacterial host as ATCC Deposit Number PTA-982. The nucleotide sequence determined by sequencing the deposited pyruvate carboxylase clone, which is shown in FIGS. 1A–C (SEQ ID NO:1), contains an open reading frame encoding a polypeptide of 1140 amino acid residues which has a deduced molecular weight of about 123.6 kDa. The 1140 amino acid sequence of the predicted pyruvate carboxylase protein is shown in FIGS. 1A–C and in SEQ ID NO:2.

Thus, one aspect of the invention provides an isolated nucleic acid molecule comprising a polynucleotide having a nucleotide sequence selected from the group consisting of: (a) a nucleotide sequence encoding the pyruvate carboxylase polypeptide having the complete amino acid sequence in SEQ ID NO:2; (b) a nucleotide sequence encoding the pyruvate carboxylase polypeptide having the complete amino acid sequence encoded by the clone contained in ATCC Deposit No. PTA-982; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 97%, 98% or 99% identical, to any of the nucleotide sequences in (a), (b) or (c) above, or a polynucleotide which hybridizes under stringent hybridization conditions to a polynucleotide having a nucleotide sequence identical to a nucleotide sequence in (a), (b) or (c), above. The polynucleotide which hybridizes does not hybridize under stringent hybridization conditions to a polynucleotide having a nucleotide sequence consisting of only A residues or of only T residues.

The present invention also relates to recombinant vectors which include the isolated nucleic acid molecules of the present invention and to host cells containing the recombinant vectors, as well as to methods of making such vectors and host cells and for using them for production of pyruvate carboxylase polypeptides or peptides by recombinant techniques.

The invention further provides an isolated pyruvate carboxylase polypeptide having amino acid sequence selected from the group consisting of: (a) the amino acid sequence of the pyruvate carboxylase polypeptide having the amino acid sequence shown in FIGS. 1A–C (SEQ ID NO:2); and (b) the amino acid sequence of the pyruvate carboxylase polypeptide having the complete amino acid sequence encoded by the clone contained in ATCC Deposit No. PTA-982. The polypeptides of the present invention also include polypeptides having an amino acid sequence with at least 90% similarity, more preferably at least 95% similarity to those described in (a) or (b) above, as well as polypeptides having an amino acid sequence at least 70% identical, more preferably at least 90% identical, and still more preferably 95%, 97%, 98% or 99% identical to those above.

BRIEF DESCRIPTION OF THE DRAWINGS

FIGS. 1A–C show the nucleotide (SEQ ID NO: 1) and deduced amino acid (SEQ ID NO:2) sequences of the complete pyruvate carboxylase protein determined by sequencing of the DNA clone contained in ATCC Deposit No. PTA-982. The protein has sequence of about 1140 amino acid residues and a deduced molecular weight of about 123.6 kDa.

DETAILED DESCRIPTION OF THE INVENTION

The present invention provides isolated nucleic acid molecules comprising a polynucleotide encoding the pyruvate carboxylase protein having the amino acid sequence shown in FIGS. 1A–C (SEQ ID NO:2) which was determined by sequencing a cloned cosmid. The pyruvate carboxylase protein of the present invention shares sequence homology with *M. tuberculosis* and human pyruvate carboxylase proteins. The nucleotide sequence shown in FIGS. 1A–C (SEQ ID NO: 1) was obtained by sequencing cosmid III F10 encoding a pyruvate carboxylase polypeptide. A clone containing the pyruvate carboxylate gene was deposited on Nov. 22, 1999 at the American Type Culture Collection, 10801 University Blvd., Manassas, Va. 20110-2209, and given accession number PTA-982.

Nucleic Acid Molecules

Unless otherwise indicated, all nucleotide sequences determined by sequencing a DNA molecule herein were determined using an automated DNA sequencer (such as the ABI Prism 377), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G , C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

Using the information provided herein, such as the nucleotide sequence in FIGS. 1A–C, a nucleic acid molecule of the present invention encoding a pyruvate carboxylase polypeptide may be obtained using standard cloning and screening procedures, such as those for cloning DNAs using mRNA as starting material. The pyruvate carboxylase protein shown in FIGS. 1A–C (SEQ ID NO:2) is about 63% identical to *M. tuberculosis* and 44% identical to human. As one of ordinary skill would appreciate, due to the possibilities of sequencing errors discussed above, as well as the variability of cleavage sites for leaders in different known proteins, the actual pyruvate carboxylase polypeptide encoded by the deposited clone comprises about 1140 amino acids, but may be anywhere in the range of 1133–1147 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 199–201 of the nucleotide sequence shown in FIGS. 1A–C (SEQ ID NO: 1); DNA molecules comprising the coding sequence for the pyruvate carboxylase protein shown in FIGS. 1A–C and SEQ ID NO:2; and DNA molecules which comprise a sequence substantially different from those described above but which, due to the degeneracy of the genetic code, still encode the pyruvate carboxylase protein. Of course, the genetic code is well known in the art. Thus, it would be routine for one skilled in the art to generate the degenerate variants described above.

In another aspect, the invention provides isolated nucleic acid molecules encoding the pyruvate carboxylase polypeptide having an amino acid sequence encoded by the clone deposited as ATCC Deposit No. PTA-982. Preferably, this nucleic acid molecule will encode the polypeptide encoded by the above-described deposited clone. The invention further provides an isolated nucleic acid molecule having the nucleotide sequence shown in FIGS. 1A–C (SEQ ID NO: 1) or the nucleotide sequence of the pyruvate carboxylase DNA contained in the above-described deposited clone, or nucleic acid molecule having a sequence complementary to one of the above sequences.

In another aspect, the invention provides an isolated nucleic acid molecule comprising a polynucleotide which hybridizes under stringent hybridization conditions to a portion of the polynucleotide in a nucleic acid molecule of the invention described above, for instance, the clone contained in ATCC Deposit PTA-982. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotide (e.g., the deposited clone), for instance, a portion 50–750 nt in length, or even to the entire length of the reference polynucleotide, also useful as probes according to the present invention, as are polynucleotides corresponding to most, if not all, of the nucleotide sequence of the deposited DNA or the nucleotide sequence as shown in FIGS. 1A–C (SEQ ID NO:1). By a portion of a polynucleotide of "at least 20 nt in length," for example, is intended 20 or more contiguous nucleotides from the nucleotide sequence of the reference polynucleotide, (e.g., the deposited DNA or the nucleotide sequence as shown in FIGS. 1A–C (SEQ ID NO: 1)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

Since a pyruvate carboxylase clone has been deposited and its determined nucleotide sequence is provided in FIGS. 1A–C (SEQ ID NO: 1), generating polynucleotides which hybridize to a portion of the pyruvate carboxylase DNA molecule would be routine to the skilled artisan. For example, restriction endonuclease cleavage or shearing by sonication of the pyruvate carboxylase clone could easily be used to generate DNA portions of various sizes which are polynucleotides that hybridize to a portion of the pyruvate carboxylase DNA molecule. Alternatively, the hybridizing polynucleotides of the present invention could be generated synthetically according to known techniques.

As indicated, nucleic acid molecules of the present invention which encode the pyruvate carboxylase protein polypeptide may include, but are not limited to those encoding the amino acid sequence of the polypeptide, by itself; the coding sequence for the polypeptide and additional sequences, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci., USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984).

The present invention further relates to variants of the nucleic acid molecules of the present invention, which encode portions, analogs or derivatives of the pyruvate carboxylase protein. Variants may occur naturally, such as a natural allelic variant. By an "allelic variant" is intended one of several alternate forms of a gene occupying a given locus on a chromosome of an organism. *Genes II,* Lewin, ed. Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and activities of the pyruvate carboxylase protein or portions thereof. Also especially preferred in this regard are conservative substitutions. Most highly preferred are nucleic acid molecules encoding the pyruvate carboxylase protein having the amino acid sequence shown in FIGS. 1A–C (SEQ ID NO:2).

Also preferred are mutants or variants whereby preferably pyruvate carboxylase is expressed 2 to 20 fold higher than its expression in *C. glutamicum* as well as feedback inhibition mutants.

Further embodiments of the invention include isolated nucleic acid molecules comprising a polynucleotide having a nucleotide sequence at least 90% identical, and more preferably at least 95%, 97%, 98% or 99% identical to (a) a nucleotide sequence encoding the pyruvate carboxylase polypeptide having the complete amino acid sequence in SEQ ID NO:2; (b) a nucleotide sequence encoding the pyruvate carboxylase polypeptide having the complete amino acid sequence encoded by the clone contained in ATCC Deposit No. PTA-9 82; or (c) a nucleotide sequence complementary to any of the nucleotide sequences in (a) or (b).

By a polynucleotide having a nucleotide sequence at least, for example, 95% "identical" to a reference nucleotide sequence encoding a pyruvate carboxylase polypeptide is intended that the nucleotide sequence of the polynucleotide is identical to the reference sequence except that the polynucleotide sequence may include up to five point mutations per each 100 nucleotides of the reference nucleotide sequence encoding the pyruvate carboxylase polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 97%, 98% or 99% identical to, for instance, the nucleotide sequence shown in FIGS. 1A–C or to the nucleotides sequence of the deposited clone can be determined conventionally using known computer programs such as the Bestfit program (Wisconsin Sequence Analysis Package, Version 8 for Unix, Genetics Computer Group, University Research Park, 575 Science Drive, Madison, Wiss. 53711). Bestfit uses the local homology algorithm of Smith and Waterman (*Advances in Applied Mathematics* 2: 482–489 (1981)) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 97%, 98% or 99% identical to the nucleic acid sequence shown in FIGS. 1A–C (SEQ ID NO: 1) or to the nucleic acid sequence of the deposited DNA, irrespective of whether they encode a polypeptide having pyruvate carboxylase activity. This is because, even where a particular nucleic acid molecule does not encode a polypeptide having pyruvate carboxylase activity, one of skill in the art would still know how to use the nucleic acid molecule, for instance, as a hybridization probe or a polymerase chain reaction (PCR) primer.

Preferred, however, are nucleic acid molecules having sequences at least 90%, 95%, 97%, 98% or 99% identical to the nucleic acid sequence shown in FIGS. 1A–C (SEQ ID NO: 1) or to the nucleic acid sequence of the deposited DNA which do, in fact, encode a polypeptide having pyruvate carboxylase protein activity. By "a polypeptide having pyruvate carboxylase activity" is intended polypeptides exhibiting activity similar, but not necessarily identical, to an activity of the pyruvate carboxylase protein of the invention as measured in a particular biological assay.

Of course, due to the degeneracy of the genetic code, one of ordinary skill in the art will immediately recognize that a large number of the nucleic acid molecules having a sequence at least 90%, 95%, 97%, 98%, or 99% identical to the nucleic acid sequence of the deposited DNA or the nucleic acid sequence shown in FIGS. 1A–C (SEQ ID NO: 1) will encode a polypeptide "having pyruvate carboxylase protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having pyruvate carboxylase protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

Vectors and Host Cells

The present invention also relates to vectors which include the isolated DNA molecules of the present invention, host cells which are genetically engineered with the recombinant vectors, and the production of pyruvate carboxylase polypeptides or portions thereof by recombinant techniques.

Recombinant constructs may be introduced into host cells using well known techniques such as infection, transduction, transfection, transvection, conjugation, electroporation and transformation. The vector may be, for example, a phage, plasmid, viral or retroviral vector.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate transacting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda $P_L$ promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating codon (AUG or GUG) at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline, ampicillin, chloramphenicol or kanamycin resistance genes for culturing in *E. coli* and other bacteria. Representative examples of appropriate hosts include bacterial cells, such as *E. coli, C. glutamicum, Streptomyces* and *Salmonella typhimurium* cells; fungal cells, such as yeast cells. Appropriate culture media and conditions for the above-described host cells are known in the art.

Among vectors preferred for use in bacteria include pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda $P_R$ and $P_L$ promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., "Basic Methods in Molecular Biology," (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The pyruvate carboxylase protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Pyruvate Carboxylase Polypeptides and Peptides

The invention further provides an isolated pyruvate carboxylase polypeptide having the amino acid sequence encoded by the deposited DNA, or the amino acid sequence in FIGS. 1A–C (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequence of the pyruvate carboxylase polypeptide can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the pyruvate carboxylase polypeptide which show substantial activity or which include regions of pyruvate carboxylase protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

The polypeptides of the present invention are preferably provided in an isolated form, and preferably are substantially purified. A recombinantly produced version of the pyruvate carboxylase polypeptide can be substantially purified by the one-step method described in Smith and Johnson, *Gene* 67:31–40 (1988).

The polypeptides of the present invention include the polypeptide encoded by the deposited DNA, the polypeptide of SEQ ID NO:2, as well as polypeptides which have at least 90% similarity, more preferably at least 95% similarity, and still more preferably at least 97%, 98% or 99% similarity to those described above. Further polypeptides of the present invention include polypeptides at least 70% identical, more preferably at least 90% or 95% identical, still more preferably at least 97%, 98% or 99% identical to the polypeptide encoded by the deposited DNA, to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2: 482–489, 1981) to find the best segment of similarity between two sequences.

By a polypeptide having an amino acid sequence at least, for example, 95% "identical" to a reference amino acid sequence of a pyruvate carboxylase polypeptide is intended that the amino acid sequence of the polypeptide is identical to the reference sequence except that the polypeptide sequence may include up to five amino acid alterations per each 100 amino acids of the reference amino acid of the pyruvate carboxylase polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 97%, 98% or 99% identical to, for instance, the amino acid sequence shown in FIGS. 1A–C (SEQ ID NO:2) or to the amino acid sequence encoded by deposited clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Genetic Tools for Manipulating Corynebacterium

To make the genetic changes necessary for metabolic engineering in *Corynebacterium*, researchers need to be able to identify and clone the genes that are involved in the target pathway. They also need methods for altering these genes to affect the regulation or level of expression of the enzymes they encode, and for subsequently reintroducing the altered genes into *Corynebacterium* to monitor their effects on amino acid biosynthesis. Therefore, metabolic engineers must have at their disposal an array of plasmids that can replicate in both *Corynebacterium* and other, more easily manipulated hosts, such as *E. coli*. Also required are a collection of selectable markers encoding, for example, antibiotic resistance, well-characterized transcriptional promoters that permit regulation of the altered genes, and efficient transformation or conjugation systems that allow the plasmids to be inserted into the target *Corynebacterium* strain.

Plasmids. Several different plasmids have been isolated and developed for the introduction and expression of genes in *Corynebacterium* (Sonnen, H., et al., *Gene* 107:69–74 (1991)). The majority of these were originally identified as small (3–5 kbp), cryptic plasmids from *C. glutamicum, C. callunae,* and *C. lactofermentum.* They fall into four compatibility groups, exemplified by the plasmids pCC1, pBL1, pHM1519, and pGA1. Shuttle vectors, plasmids that are capable of replicating in both *Corynebacterium* and *E. coli,* have been developed from these cryptic plasmids by incorporating elements from known *E. coli* plasmids (particularly the ColE1 origin of replication from pBR322) or pUC 18), as well as antibiotic-resistance markers. A fifth class of plasmids that is very useful for manipulating *Corynebacterium* is based on pNG2, a plasmid originally isolated from *Corynebacterium diphtheriae* (Serwold-Davis, T. M., et al., *Proc. Natl. Acad. Sci. USA* 84:4964–4968 (1987)). This plasmid and its derivatives replicate efficiently in many species of *corynebacteria,* as well as in *E. coli.* Since the sole origin of replication in pNG2 (an element of only 1.8 kbp) functions in both the Gram-positive and Gram-negative host, there is no need to add an additional ColE1-type element to it. As a result, pNG2 derivatives (e.g., pEP2) are much smaller than other *Corynebacterium* shuttle vectors and are therefore more easily manipulated.

Selectable Markers. Several genes conferring antibiotic resistance have proven useful for plasmid selection and in other recombinant DNA work in *corynebacteria*. These include the kanamycin resistance determinant from Tn903, a hygromycin resistance marker isolated from *Streptomyces hygroscopicus,* a tetracycline resistance gene from *Streptococcus faecalis,* a bleomycin resistance gene from Tn5, and a chloramphenicol resistance marker from *Streptomyces acrimycini.* The β-lactamase gene that is employed in many *E. coli* plasmids such as pBR322 does not confer ampicillin resistance in *Corynebacterium.*

Transformation Systems. Several methods have been devised for introducing foreign DNA into *Corynebacterium.* The earliest method to be employed routinely was based on protocols that had been successful for other Gram-positive species involving incubation of spheroplasts in the presence of DNA and polyethylene glycol (Yoshihama, M., et al., *J. Bacteriol.* 162:591–597 (1985)). While useful, these methods were generally inefficient, often yielding fewer than $10^5$ transformants per milligram of DNA. Electroporation of *Corynebacterium* spheroplasts has proven to be a much more efficient and reliable means of transformation. Spheroplasts are generated by growing the cells in rich media containing glycine and/or low concentrations of other inhibitors of cell wall biosynthesis, such as isonicotinic acid hydrazide (isoniazid), ampicillin, penicillin G, or Tween-80. The spheroplasts are then washed in low-salt buffers containing glycerol, concentrated, and mixed with DNA before being subjected to electroporation. Efficiencies as high as $10^7$ transformants per microgram of plasmid DNA have been reported with this protocol.

A third method for DNA transfer into corynebacteria involves transconjugation. This method takes advantage of the promiscuity of *E. coli* strains carrying derivatives of the plasmid RP4. In *E. coli*, RP4 encodes many functions that mediate the conjugal transfer of plasmids from the host strain to other recipient strains of *E. coli*, or even to other species. These "tra functions" mediate pilus formation and plasmid transfer. RP4 also carries an origin of transfer, oriT, a cis-acting element that is recognized by the transfer apparatus that allows the plasmid to be conducted through the pilus and into the recipient strain. From this system Simon et al. (*Bio/Technology* 1:784–791 (1985)) have developed a useful transconjugation tool that allows the transfer of plasmids from *E. coli* to *Corynebacterium*. They relocated the tra functions from RP4 into the *E. coli* chromosome in a strain called S17-1. Plasmids carrying the RP4 oriT can be mobilized from S17-1 into other recipients very efficiently. Although this method has proven useful for introducing replicating plasmids into *Corynebacterium*, it has proven even more useful for generating gene disruptions. This is accomplished by introducing a selectable marker into a clone of the *Corynebacterium* gene that is targeted for disruption. This construct is then ligated into an *E. coli* plasmid that carries the RP4 oriT but lacks an origin to support replication in *Corynebacterium*. S17-1 carrying this plasmid is then incubated with the recipient strain and the mixture is later transferred to a selective medium. Because the plasmid that was introduced is unable to replicate in *corynebacteria*, transconjugants that express the selectable marker are most likely to have undergone a cross-over recombination within the genomic DNA.

Restriction-Deficient Strains. Regardless of the transformation system used, there is clear precedent in the literature that *corynebacteria* are able to recognize *E. coli*-derived DNA as foreign and will most often degrade it. This ability has been attributed to the *Corynebacterium* restriction and modification system. To overcome this system, some transformation and transconjugation protocols call for briefly heating the recipient strain prior to transformation. The heat treatment presumably inactivates the enzymes responsible for the restriction system, allowing the introduced DNA to become established before the enzymes are turned over. Another strategy for improving the efficiency of DNA transfer has been to isolate *Corynebacterium* mutants that are deficient in the restriction system. These strains will incorporate plasmids that had been propagated in *E. coli* with almost the same efficiency as plasmids that had been propagated in *Corynebacterium*. In an alternate strategy used to circumvent the restriction system in *Corynebacterium*, Leblon and coworkers (Reyes, O., et al., *Gene* 107:61–68 (1991)) developed an "integron" system for gene disruption. Integrons are DNA molecules that have the same restriction/modification properties as the target host's DNA, carry DNA that is homologous to a portion of the host genome (i.e., a region of the genome that is to be disrupted), and are unable to replicate in the host cell. A cloned gene from *Corynebacterium* is first interrupted with a selectable marker in a plasmid that is propagated in one *Cornynebacterium* strain. This construct is then excised from the *corynebacterial* plasmid and self-ligated to form a non-replicating circular molecule. This "integron" is then electroporated into the restrictive host. Modification of the DNA allows the integron to elude the host restriction system, and recombination into the host genome permits expression of the selectable marker.

Promoters. Reliable transcriptional promoters are required for efficient expression of foreign genes in *Corynebacterium*. For certain experiments, there is also a need for regulated promoters whose activity can be induced under specific culture conditions. Promoters such as the fda, thrC, and hom promoters derived from *Corynebacterium* genes have proven useful for heterologous gene expression. Inducible promoters from *E. coli*, such as $P_{lac}$, and $P_{trc}$, which are induced by isopropylthiogalactopyranoside (IPTG) when the lac repressor (lacI) is present; $P_{trp}$, which responds to the inducer indole acrylic acid when the trp repressor (trpR) is present; and lambda $P_L$, which is repressed in the presence of the temperature-sensitive lambda repressor (cI857), have all been used to modulate gene expression in *Corynebacterium*.

Gene Identification. With all other genetic tools in place, there still remains the challenge of identifying relevant genes from Corynebacterium. In *E. coli*, some of the resources that have been used to isolate genes are transducing phage, transposable elements, genetic maps of the *E. coli* chromosome from transduction and transconjugation experiments, and more recently, complete physical and sequence maps of the chromosome. To date, the most successful method for identifying and recovering genes from *Corynebactrium* has been to use *Corynebactrium* genomic DNA to complement known auxotrophs of *E. coli*. In this exercise, libraries of plasmids carrying fragments of the *Corynebactrium* genome are introduced into *E. coli* strains that are deficient in a particular enzyme or function. Transformants that no longer display the auxotrophy (e.g., homoserine deficiency) are likely to carry the complementing gene from *Corynebactrium*. This strategy has led to isolation of numerous *Corynebactrium* genes, including several from the pathways responsible for synthesis of aspartate-derived and aromatic amino acids, intermediary metabolism, and other cellular processes. One limitation to this strategy is that not all genes from *Corynebactrium* will be expressed in the *E. coli* host. Thus, although a gene may be represented in the plasmid library, it may be unable to complement the *E. coli* mutation and therefore would not be recovered during selection. Overcoming this limitation, a smaller number of genes have been identified with a similar strategy in which a plasmid library from wild-type *Corynebactrium* was used to directly complement mutations in other *Corynebacterium* strains. Although this strategy avoids the concern of insufficient gene expression in the auxotrophic host, its utility is limited by poor plasmid-transformation efficiency in the auxotrophs. Still other genes have been identified by hybridization with nucleic acid probes based upon homologous genes from other species, and direct amplification of genes using the polymerase chain reaction and degenerate oligonucleotide primers.

Transposable Elements. Transposable elements are extremely powerful tools in gene identification because they couple mutagenesis with gene recovery. Unlike classical mutagenesis techniques, which generate point mutations or small deletions within a gene, when transposable elements insert within a gene they form large disruptions, thereby "tagging" the altered gene for easier identification. A number of transposable elements have been found to transpose in *Corynebactrium*. Transposons found in the plasmids pTP10 of *C. xerosis* and pNG2 of *C. diphtheriae* have been shown to transpose in *C. glutamicum* and confer resistance to erythromycin. A group from the Mitsubishi Chemical Company in Japan developed a series of artificial transposons from an insertion sequence, IS31831, that they discovered in *C. glutamicum* (Vertes, A. A., et al., *Mol. Gen. Genet.* 245:397–405 (1994)). After inserting a selectable marker between the inverted repeats of IS31831, these researchers were able to introduce the resulting transposon into *C. glutamicum* strains on an *E. coli* plasmid (unable to replicate in *Corynebactrium*) via electroporation. They found that the selectable marker had inserted into the genome of the target cell at a frequency of approximately $4 \times 10^4$ mutants/µg DNA. The use of such transposons to generate *Corynebactrium* auxotrophs has led to the isolation of several genes responsible for amino acid biosynthesis, as well as other functions in *corynebacteria*.

Transducing Phage. Transducing phage have been used in other systems for mapping genetic loci and for isolating genes. In 1976, researchers at Ajinomoto Co. in Japan surveyed 150 strains of characterized and uncharacterized strains of glutamic acid-producing coryneform bacteria to identify phage that might be useful for transduction (Mornose, H., et al., *J. Gen. Appl. Microbiol. Rev.* 16:243–252 (1995)). Of 24 different phage isolates recovered from this screen, only three were able to transduce a trp marker from a trp$^+$ donor to a trp$^-$ recipient with any appreciable frequency, although even this efficiency was only $10^{-7}$ or less. These researchers were able to improve transduction efficiency slightly by including 4 mM cyclic adenosine monophosphate (cAMP) or 1.2 M magnesium chloride. Several different researchers have attempted to develop reliable transduction methods by isolating corynephages from sources such as contaminated industrial fermentations, soil, and animal waste. Although many phage have been isolated and characterized, few have been associated with transduction, and an opportunity still exists to develop a reliable, high-efficiency transduction system for general use with the glutamic acid-producing bacteria.

EXAMPLES

The following protocols and experimental details are referenced in the examples that follow.

Bacterial Strains and Plasmids *C. glutamicum* 21253 (hom$^-$, lysine overproducer) was used for the preparation of chromosomal DNA. *Escherichia coli* DH5α (hsdR$^-$, recA$^-$) (Hanahan, D., *J. Mol. Biol.* 166:557–580 (1983)) was used for transformations. Plasmid pCR2.1 TOPO (Invitrogen) was used for cloning polymerase chain reaction (PCR) products. The plasmid pRR850 was constructed in this study and contained an 850-bp PCR fragment cloned in the pCR2.1 TOPO plasmid.

Media and Culture Conditions

*E. coli* strains were grown in Luria-Bertani (LB) medium at 37° C. (Sambrook, J., et al., *Molecular Cloning: a Laboratory Manual*, 2nd edn., Cold Spring Harbor Laboratory, Cold Spring Harbor, N.Y. (1989)). *C. glutamicum* was grown in LB medium at 30° C. Where noted, ampicillin was used at the following concentrations: 100 µg/ml in plates and 50 µg/ml in liquid culture.

DNA Manipulations

Genomic DNA was isolated from *C. glutamicum* as described by Tomioka et al. (Tomioka, N., et al., *Mol. Gen. Genet.* 184:359–363 (1981)). PCR fragments were cloned into the pCR2.1 TOPO vector following the manufacturer's instructions. Cosmid and plasmid DNA were prepared using Qiaprep spin columns and DNA was extracted from agarose gels with the Qiaex kit (Qiagen). For large-scale high-purity preparation of cosmid DNA for sequencing, the Promega Wizard kit was used (Promega). Standard techniques were used for transformation of *E. coli* and agarose gel electrophoresis (Sambrook, J., et al., *Molecular cloning: a laboratory manual*, 2nd edn., Cold Spring Harbor Laboratory, Cold Spring Harbor, N.Y. (1989)). Restriction enzymes were purchased from Boehringer Mannheim or New England Biolabs.

Cosmid Library

The cosmid library used was constructed by cloning *C. glutamicum* chromosomal DNA into the Supercos vector (Stratagene).

Polymerase Chain Reaction (PCR)

PCR was performed using the Boehringer Mannheim PCR core kit following the manufacturer's instructions. When PCR was performed on *Corynebacterium* chromosomal DNA, about 1 µg DNA was used in each reaction. The forward primer used was 5'GTCTTCATCGAGATGAATC-CGCG3' (SEQ ID NO:3) and the reverse primer used was 5'CGCAGCGCCACATCGTAAGTCGC3' (SEQ ID NO:4) for the PCR reaction.

Dot-Blot Analysis

Dot blots containing DNA from cosmids identified in this study and the probe as a positive control were prepared using the S&S (Schleicher & Schüll) minifold apparatus An 850-bp fragment encoding a portion of the *C. glutamicum* pyruvate carboxylate gene was used as the probe. The probe was labeled with digoxigenin-11-dUTP (Boehringer Mannheim) in a randomly primed DNA-labeling reaction as described by the manufacturer. Hybridization, washing and calorimetric detection of the dot blots were done with the Genius system from Boehringer following the protocols in their user's guide for filter hybridization. The initial hybridization with the 291 cosmids was carried out at 65° C. overnight and washes were performed at the hybridization temperature. For the 17 cosmids that were used in the second screen, the hybridization was carried out at 65° C., but for only 8 h, and the time of exposure to the film was decreased.

Detection of Biotin-containing Proteins by Western Blotting

Cell extracts from *C. glutamicum* were prepared as described by Jetten and Sinskey (Jetten, M. S. M., & Sinskey, A. J., *FEMS Microbiol. Lett.* 111:183–188 (1993)). Proteins in cell extracts were separated in sodium dodecyl sulfate (SDS)/7.5% polyacrylamide gels in a BioRad mini gel apparatus and were electroblotted onto nitro-cellulose, using the BioRad mini transblot apparatus described by Towbin et al. (Towbin, H., et al., *Proc. Natl. Acad. Sci. USA* 76:4350–4354 (1979)). Biotinylated proteins were detected using avidin-conjugated alkaline phosphatase from BioRad and 5-bromo-4-chloro-3-indoylphosphate-p-toludine salt/nitroblue tetrazolium chloride from Schleicher & Schüll.

DNA Sequencing

Automated DNA sequencing was performed by the MIT Biopolymers facility employing an ABI Prism 377 DNA sequencer.

Sequence Analysis

The program DNA Strider Version 1.0 (Institut de Recherche Fondamentale, France) was used to invert, complement and translate the DNA sequence, and find open-reading frames in the sequence. The BLAST program (Altschul, S. F., et al., *J. Mol. Biol.* 215:403–410 (1990)) from the National Center for Biotechnology Information (NCBI) was employed to compare protein and DNA sequences. Homology searches in proteins were done using the MACAW software (NCBI). PCR primers were designed with the aid of the Primer Premier software from Biosoft International. The compute pI/MW tool on the ExPasy molecular biology server (University of Geneva) was used to predict the molecular mass and pI of the deduced amino acid sequence.

Example 1

Western Blotting to Detect Biotinylated Enzymes

Since pyruvate carboxylate is known to contain biotin, Western blotting was used to detect the production of biotinylated proteins by *C. glutamicum*. Two biotinylated proteins were detected in extracts prepared from cells grown in LB medium, (data not shown) consistent with previous reports. One band, located at approximately 80 kDa, has been identified as the biotin-carboxyl-carrier domain (BCCP) of the acetyl-CoA carboxylase (Jager, W., et al., *Arch. Microbiol.* 166:76–82 (1996)). The second band, at 120 kDa, is believed to be the pyruvate carboxylase enzyme, as these proteins are in the range 113–130 kDa (Attwood, P. V., *Int. J. Biochem. Cell. Biol.* 27:231–249 (1995)).

Example 2

PCR and Cloning

*C. glutamicum* pyruvate carboxylase gene was cloned on the basis of the homology of highly conserved regions in previously cloned genes. Pyruvate carboxylase genes from thirteen organisms were examined and primers corresponding to an ATP-binding submotif conserved in pyruvate carboxylases and the region close to the pyruvate-binding motif (Table 1) were designed. Where the amino acids were different the primers were designed on the basis of *M. tuberculosis* because of its close relationship to *C. glutamicum*. An 850-bp fragment was amplified from *C. glutamicum* genomic DNA using the PCR and cloned in the pCR2.1 TOPO vector of Invitrogen to construct plasmid pRR850. Primers were also designed based on the conserved biotin-binding site and pyruvate-binding site (data not shown).

Example 3

Isolating a Cosmid Containing the *C. glutamicum* Pyruvate Carboxylase Gene

The 850-base-pair fragment containing a portion of the *C. glutamicum* pyruvate carboxylase gene was used to probe a *C. glutamicum* genomic library. In the first round of screening, 17 out of 291 cosmids in a dot blot appeared positive. A second round of screening was performed on these 17 cosmids, using the same probe but more stringent hybridization conditions, yielding four cosmids with a positive signal. To confirm that these cosmids indeed contained the pyruvate carboxylase gene, PCR was performed using the four positive cosmids as templates and the same primers used to make the probe. An 850-bp fragment was amplified from all four positive cosmids, designated IIIF10, IIE9, IIIG7 and IIIB7.

TABLE 1

Pyruvate carboxylase sequences from 13 organisms (obtained from GenBank) were aligned using the MACAW software. Two highly conserved regions were selected and oligonucleotide primers were designed on the basis of the *Mycobacterium tuberculosis* DNA sequence corresponding to these regions. The forward primer was based on the DNA sequence corresponding to conserved region A and the reverse primer was based on the DNA sequence corresponding to conserved region B.

| Organism | Conserved region A | Conserved region B |
|---|---|---|
| Caenorhabditis elegans | YFIEVNAR (SEQ ID NO:5) | ATFDVSM (SEQ ID NO:6) |
| Aedes aegypti | YFIEVNAR (SEQ ID NO:7) | ATFDVAL (SEQ ID NO:8) |
| Mycobacterium tuberculosis | VFIEMNPR (SEQ ID NO:9) | ATYDVAL (SEQ ID NO:10) |
| Bacillus stearothermophilus | YFIEVNPR (SEQ ID NO:11) | ATFDVAY (SEQ ID NO:12) |
| Pichia pastoris | YFIEINPR (SEQ ID NO:13) | ATFDVSM (SEQ ID NO:14) |
| Mus musculus | YFIEVNSR (SEQ ID NO:15) | ATFDVAM (SEQ ID NO:16) |
| Rattus norvegicus | YFIEVNSR (SEQ ID NO:17) | ATFDVAM (SEQ ID NO:18) |
| Saccharomyces cerevisiae 1 | YFIEINPR (SEQ ID NO:19) | ATFDVAM (SEQ ID NO:20) |
| Saccharomyces cerevisiae 2 | YFIEINPR (SEQ ID NO:21) | ATFDVAM (SEQ ID NO:22) |
| Rhizabium etli | YFIEVNPR (SEQ ID NO:23) | ATFDVSM (SEQ ID NO:24) |
| Homo sapiens | YFIEVNSR (SEQ ID NO:25) | ATFDVAM (SEQ ID NO:26) |
| Schizosaccharomyces pombe | YFIEINPR (SEQ ID NO:27) | ATFDVSM (SEQ ID NO:28) |

Table 1 Pyruvate carboxylase sequences from 13 organisms (obtained from GeneBank) were aligned using the MACAW software. Two highly conserved regions were selected and oligonucleotide primers were designed on the basis of the *Mycobacterium tuberculosis* DNA sequence corresponding to these regions. The forward primer was based on the DNA sequence corresponding to conserved region A and the reverse primer was based on the DNA sequence corresponding to conserved region B.

Example 4

Sequencing Strategy

The 850-bp insert of plasmid pRR850 was sequenced using the M13 forward and M13 reverse primers. On the basis of this sequence, primers Begrev1 and Endfor1 were designed and used to sequence outwards from the beginning and the end of the 850-bp portion of the pyruvate carboxylase gene. Cosmid III F10 was used as the sequencing template. The sequencing was continued by designing new primers (Table 2) and "walking" across the gene.

Example 5

Sequence Analysis 3637 bp of cosmid III F10 were sequenced. A 3420-bp open reading frame was identified, which is predicted to encode a protein of 1140 amino acids. The deduced protein is 63% identical to *M. tuberculosis* pyruvate carboxylase and 44% identical to human pyruvate carboxylase, and the *C. glutamicum* gene pc was named on the basis of this homology. The deduced protein has a predicted pI of 5.4 and molecular mass of 123.6 kDa, which is similar to the subunit molecular mass of 120 kDa estimated by SDS/polyacrylamide gel electrophoresis. Upstream of the starting methionine there appears to be a consensus ribosome binding-site AAGGAA. The predicted translational start site, based on homology to the *M. tuberculosis* sequence, is a GTG codon, as has been observed in other bacterial sequences (Stryer, L., *Biochemistry*, 3rd edn., Freeman, N.Y. (1988); Keilhauer, C., et al., *J. Bacteriol.* 175:5595–5603 (1993)). The DNA sequence has been submitted to GenBank and has been assigned the accession number AF038548.

The amino-terminal segment of the *C. glutamicum* pyruvate carboxylase contains the hexapeptide GGGGRG (SEQ IID NO:37), which matches the GGGG(R/K)G (SEQ ID NO:38) sequence that is found in all biotin-binding proteins and is believed to be an ATP-binding site (Fry, D.C., et al., *Proc. Natl. Acad. Sci. USA* 83:907–911 (1986); Post, L.E., et al., *J. Biol. Chem.* 265:7742–7747 (1990)). A second region that is proposed to be involved in ATP binding and is present in biotin-dependent carboxylases and carbamyphosphate synthetase (Lim, F., et al., *J. Biol. Chem.* 263:11493–11497 (1988)) is conserved in the *C. glutamicum* sequence. The predicted *C. glutamicum* pyruvate carboxylase protein also contains a putative pyruvate-binding motif, FLFEDPWDR (SEQ ID NO:29), which is conserved in the transcarboxylase domains of *Mycobacterium, Rhizobium* and human pyruvate carboxylases (Dunn, M. F., et al., *J. Bacteriol.* 178:5960–5970 (1996)). Tryptophan fluorescence studies with transcarboxylase have shown that the Trp residue present in this motif is involved in pyruvate binding (Kumer, G. K., et al., *Biochemistry* 27:5978–5983 (1988)). The carboxy-terminal segment of the enzyme contains a putative biotin-binding site, AMKM (SEQ ID NO:39), which is identical to those found in other pyruvate carboxylases as well as the biotin-carboxyl-carrier protein (BCCP) domains of other biotin-dependent enzymes.

TABLE 2

DNA sequences of the primers used to obtain the sequence of the pyruvate carboxylase gene in the cosmid IIIF10

| Primer name | Primer sequence (5'–3') |
|---|---|
| Begrev1 | TTCACCAGGTCCACCTCG (SEQ ID NO:30) |
| Endfor1 | CGTCGCAAAGCTGACTCC (SEQ ID NO:31) |
| Begrev2 | GATGCTTCTGTTGCTAATTTGC (SEQ ID NO:32) |
| Endfor2 | GGCCATTAAGGATATGGCTG (SEQ ID NO:33) |
| Begrev3 | GCGGTGGAATGATCCCCGA (SEQ ID NO:34) |
| Endfor3 | ACCGCACTGGGCCTTGCG (SEQ ID NO:35) |
| Endfor4 | TCGCCGCTTCGGCAACAC (SEQ ID NO:36) |

Table 2 DNA sequences of the primers used to obtain the sequence of pyruvate carboxylase gene in the cosmid IIIF10

Previous studies have shown that phosphoenolpyruvate carboxylase (ppc) is not the main anaplerotic enzyme for *C. glutamicum*, since its absence does not affect lysine production (Gubler, M., et al., *Appl. Microbiol. Biotechnol.* 40:857–863 (1994); Peters-Wendisch, P. G., et al., *Microbiol. Lett.* 112:269–274 (1993)). Moreover, a number of studies have indicated the presence of a pyruvate-carboxylating enzyme, employing $^{13}$C-labeling experiments and NMR and GC-MS analysis (Park, S. M., et al., *Applied Microbiol. Biotechnol.* 47:430–440 (1997b); Peters-Wendisch, P. G., et al., *Arch. Microbiol.* 165:387–396 (1996)), or enzymatic assays with cell free extracts (Tosaka, O., *Agric. Biol. Chem.* 43:1513–1519 (1979)) and permeable cells (Peters-Wendisch, P. G., et al., *Microbiol.* 143:1095–1103 (1997)). Very low pyruvate carboxylation activity were detected in cell-free extracts, but this activity was not uncoupled from a very high ATP background. It is highly probable that the activity measured is due to reversible gluconeogenic enzymes, such as oxaloacetate decarboxylase and malic enzyme. The presence of pyruvate carboxylase in *C. glutamicum* makes it highly unlikely that the gluconeogenic enzymes mentioned above can serve the anaplerotic needs of this strain.

The deduced amino acid sequence of the *C. glutamicum* pyruvate carboxylase gene has significant similarity to the pyruvate carboxylase sequences from a diverse group of organisms. It contains a biotin carboxylase domain in its N-terminal region, a BCCP domain in its C-terminal region, and a transcarboxylase domain with a binding site specific for pyruvate in its central region. The *C. glutamicum* pyruvate carboxylase protein showed strong homology to *M. tuberculosis* and the human pyruvate carboxylase (Wexler, I. D., et al., *Biochim. Biophys. Acta* 1227:46–52 (1994)).

There are precedents to finding that *C. glutamicum* contains more than one enzyme to perform the anaplerotic function of regenerating oxaloacetate. *Pseudomonas citronellolis, Pseudomonas fluorscens, Azotobacter vinelandii* and *Thiobacillus novellus* contain both ppc and pyruvate carboxylase (O'Brien, R. W., et al., *J. Biol. Chem.* 252:1257–1263 (1977); Scrutton, M. C. and Taylor, B. L., *Arch. Biochem. Biophys.* 164:641–654 (1974); Milrad de Forchetti, S. R., & Cazullo, J. J., *J. Gen. Microbiol.* 93:75–81 (1976); Charles, A. M., & Willer, D. W., *Can. J. Microbiol.* 30:532–539 (1984)). *Zea mays* contains three isozymes of ppc (Toh, H., et al., *Plant Cell Environ.* 17:31–43 (1994)) and *Saccharomyces cerevisiae* contains two isozymes of pyruvate carboxylase (Brewster, N. K., et al., *Arch. Biochem. Biophys.* 311:62–71 (1994)), each differentially regulated. With the present discovery of the existence of a pyruvate carboxylase gene in *C. glutamicum*, the number of enzymes that can interconvert phosphoenolpyruvate (PEP), oxaloacetate and pyruvate in this strain rises to six. This presence of all six enzymes in one organism has not been reported previously. *P. citronellolis* contains a set of five enzymes that interconvert oxaloacetate, PEP and pyruvate, namely pyruvate kinase, PEP synthetase, PEP carboxylase, oxaloacetate decarboxylase and pyruvate carboxylase (O'Brien, R. W., et al., *J. Biol. Chem.* 252:1257–1263 (1977)). Azotobacter contains all of the above enzymes except PEP synthetase (Scrutton, M. C., & Taylor, B. L., *Arch. Biochem. Biophys.* 164:641–654 (1974)).

The presence in *C. glutamicum* of the six metabolically related enzymes suggests that the regulation of these enzymes through effectors is important. Biochemical and genetic study of all six enzymes in coordination with other downstream activities may lead to the elucidation of the exact procedures necessary for maximizing the production of primary metabolites by this industrially important organism.

Example 6

Construction of a Pyruvate Carboxylase Mutant

The entire reading frame from nucleotide 180 to nucleotide 3630 of the pyruvate carboxylase DNA was amplified using PCR. The oligonucleotide primers used for the PCR were designed to remove the SalI site within the coding sequence by silent mutagenesis and introduce EcoRV and SalI sites upstream and downstream, respectively, of the open reading frame. The PCR product was digested with EcoRV and SalI and cloned into the vector pBluescript. The resulting plasmid is pPCBluescript. To obtain a plasmid-borne disruption of pyc, a derivative of pPCBluescript was constructed in which the middle portion of the pyc gene was deleted and replaced with the tsr gene, which encodes resistance to the antibiotic thiostrepton. The RP4 mob element was then inserted into the plasmid, yielding pAL240. This plasmid can be conjugally transferred into *Corynebactrium*, but it is then unable to replicate because it has only a ColE1 origin of replication. pAL240 was transferred from *E. coli* S17-1 into *C. glutamicum* via transconjugation, and transconjugants were selected on medium containing thiostrepton and nalidixic acid.

After the drug resistance phenotype of each transconjugant was confirmed, the transconjugants were tested for their ability to grow on different carbon sources. Because pAL240 cannot replicate in *C. glutamicum,* the only cells which will survive should be those whose genomes have undergone recombination with the plasmid. Several candidates were identified with the proper set of phenotypes: they are resistant to thiostrepton and nalidixic acid, grow well on minimal plates containing glucose or acetate as the sole carbon source, and grow poorly or not at all on minimal plates containing lactate as the sole carbon source. Southern hybridization and PCR-based assays are used to confirm whether there is only one copy of the pyruvate carboxylase gene in the genome and that it is disrupted with the thiostrepton resistance marker. Lysine production and the production of biotinylated proteins by this strain is examined, and the Δpyc strain as a negative control in activity assays and as a host strain for complementation tests.

Example 7

Development of an Overexpressing Strain

In order to test the hypothesis that increased levels of pyruvate carboxylase will lead to increased production of lysine, it is necessary to construct strains in which expression of the pyruvate carboxylase gene is under the control of an inducible promoter.

The vector pAPE12, which has the NG2 origin of replication and a multiple cloning site downstream of the IPTG-controlled trc promoter, was used as an expression vector in *C. glutamicum*. A derivative of pAPE12 was constructed which contained the pyruvate carboxylase gene downstream of Ptrc. The pyc gene was excised from pPCBluescript using SalI and XbaI and ligated into pAPE12 which had been cleaved with the same enzymes, forming pLW305. The pyruvate carboxylase gene present in PCBluescript (and hence in pLW305) has the wild type GTG start codon, and the SalI restriction site present near the 5' end of the wild type gene was eliminated by the introduction of a one base silent mutation during amplification of the pyruvate carboxylase gene.

pLW305 and pAPE12 was electroporated into several other *Corynebactrium* genetic backgrounds.

Because the pyruvate carboxylase gene in pLW305 has a GTG start codon and carries some intervening DNA between the trc promoter and the start codon, a pyruvate carboxylase overexpression plasmid, pXL1, was designed that eliminates those shortcomings. The 5' end of the gene was amplified from pLW305 with oligonucleotide primers that simultaneously change the GTG start codon to ATG and introduce a BspLU11-I restriction site, which is compatible with NcoI. The PCR product was then cut with BspLU11-I and AfeI, and ligated into the 7.5 kb backbone obtained by partial digest of pLW305 with NcoI followed by complete cutting with AfeI. Two independent sets of ligations and transformations have yielded putative pXL1 clones.

Example 8

Fermentation Results

It has been shown that the level of pyruvate carboxylase activity varies greatly with the carbon source used when the gene is expressed from its native *C. glutamicum* promoter. Therefore, production of pyruvate carboxylase in strains grown on these carbon sources was examined.

The strains NRRL B-11474, NRRL B-11474 (pLW305), and NRRL B-11474 Δpyc candidate 35 were cultured in flasks on minimal medium for NRRL B-11474 with two different sources of carbon: glucose or lactate. The results on growth and amino acid production are presented below.

|  | glucose | | | lactate | | |
| --- | --- | --- | --- | --- | --- | --- |
|  | biomass (g/l) | lysine (g/l) | Y lys/glc (g/g) | biomass (g/l) | lysine (g/l) | Y lys/lac (g/g) |
| NRRL B-11474 | 6.7 ± 0.2 | 5.0 ± 0.7 | 0.21 | 3 | 1.7 | 0.12 |
| NRRL B-11474 (pLW305) | 7.3 ± 0.2 | 5.3 ± 0.2 | 0.22 | 4 | 2.5 | 0.15 |
| Δpyc #35 | 1.1 | 0 | 0 | 0 | 0 | 0 |

NRRL B-11474 and pLW305 show the same behavior on glucose. Both strains produce the same amount of biomass and lysine. On lactate the strains also have similar yield of lysine. NRRL B-11474 (pLW305) consumed all of the lactate in the medium (17 g/l) whereas the wild type NRRLB-11474 consumed 40% less lactate during the same period of time. The NRRL B-11474 was calculated to consume lactate at a rate of 0.37 g lactate/hour, whereas the NRRL B-11474 (pLW305) strain consumed this substrate at a rate of 0.65 g lactate/hour.

The NRRL B-11474 Δpyc doesn't grow on lactate, which is consistent with the expected phenotype. Its growth on glucose is very low and the strain does not produce lysine. Kinetic studies are conducted to characterize further the behavior of these strains.

Example 9

Visualization of Biotinylated Proteins

Pyruvate carboxylase contains biotin. Therefore, it should be possible to detect the accumulation of this enzyme by monitoring the appearance of specific biotinylated products in cells.

Example 10

Electrophoretic Gels

To detect biotinylated proteins in electrophoretic gels, a commercially available streptavidin linked to alkaline phosphatase was used. Crude protein lysates from induced and uninduced cultures of *E. coli* DH5α or NRRL B-11474 harboring pAPE12 or pLW305 and separated the proteins on duplicate 7.5% polyacrylamide denaturing electrophoretic gels. One gel of each pair is stained with Coomassie Brilliant Blue to visualize all proteins and ensure equal levels of protein were loaded in each lane. The other gels are treated with the streptavidin-alkaline phosphatase reagent, which binds to biotinylated proteins. The location of these proteins can then be visualized by providing alkaline phosphatase with a colorimetric substrate, 5-bromo-4-chloro-3-indolyl phosphate (BCIP). As reported by others, two major biotinylated proteins were detected. The higher molecular weight species (approx. 120 kDa) has been shown to be pyruvate carboxylase, and the lower molecular weight species (approx. 60 kDa) is the biotinylated subunit of acetyl-CoA carboxylase.

All publications mentioned hereinabove are hereby incorporated in their entirety by reference.

While the foregoing invention has been described in some detail for purposes of clarity and understanding, it well be appreciated by one skilled in the art from a reading of this disclosure that various changes in form and detail can be made without departing from the true scope of the invention and appended claims.

What is claimed is:

1. A method of making lysine by fermentation, comprising culturing a strain of *Corynebacterium glutamicum* in a culture medium, said strain including a nucleic acid molecule encoding pyruvate carboxylase, said nucleic acid molecule comprising a polynucleotide having a nucleotide sequence at least 95% identical to a sequence selected from the group consisting of:

(a) a nucleotide sequence encoding the pyruvate carboxylase polypeptide having the amino acid sequence of SEQ ID NO: 2;

(b) a nucleotide sequence encoding the pyruvate carboxylase polypeptide having the complete amino acid sequence encoded by the clone contained in ATCC Deposit No. PTA-982; and (c) a nucleotide sequence complementary to any of the nucleotide sequences in (a) or (b), wherein said pyruvate carboxylase is expressed 2 to 20 fold higher in said strain than in wild-type *Corynebacterium glutamicum*;

producing lysine, and recovering said lysine.

* * * * *